United States Patent [19]
Kadowaki et al.

[11] Patent Number: 5,626,822
[45] Date of Patent: *May 6, 1997

[54] CASH TRANSACTION MACHINE AND METHOD THEREFOR

[75] Inventors: Minoru Kadowaki, Toyota; Atsuko Uozumi, Owariasahi; Ryozo Nakamura, Aichi-ken; Riichi Kato, Owariasahi; Kousuke Noda, Tsuchiura; Hiroyuki Kashiwada, Nagoya; Yoshio Horiba; Takashi Hanamura, both of Seto, all of Japan

[73] Assignee: Hitachi, Ltd., Tokyo, Japan

[*] Notice: The term of this patent shall not extend beyond the expiration date of Pat. No. 5,578,281.

[21] Appl. No.: 430,801

[22] Filed: Apr. 26, 1995

Related U.S. Application Data

[63] Continuation-in-part of Ser. No. 297,093, Aug. 26, 1994, Pat. No. 5,578,281, and Ser. No. 310,379, Sep. 22, 1994, Pat. No. 5,504,313, which is a division of Ser. No. 637,785, Jan. 7, 1991, Pat. No. 5,374,814.

[30] Foreign Application Priority Data

| Jan. 12, 1990 | [JP] | Japan | 2-003585 |
| Sep. 3, 1990 | [JP] | Japan | 2-233017 |
| Aug. 27, 1993 | [JP] | Japan | 5-212487 |
| Dec. 16, 1993 | [JP] | Japan | 5-316267 |
| Nov. 10, 1994 | [JP] | Japan | 6-276377 |

[51] Int. Cl.$^6$ .................. B01B 1/00; A61L 2/04
[52] U.S. Cl. .......... 422/307; 235/7 R; 235/379; 422/291; 134/122 R
[58] Field of Search .......... 422/5, 24, 307, 422/291; 235/7 R, 379; 134/122 R

[56] References Cited

U.S. PATENT DOCUMENTS

| 1,579,124 | 3/1926 | MacGarth | 235/7 R |
| 3,779,791 | 12/1973 | Ploetz et al. | 21/58 |
| 4,449,050 | 5/1984 | Kamhi | |
| 4,697,071 | 9/1987 | Hiraoka et al. | |
| 4,972,958 | 11/1990 | Ito et al. | |
| 5,021,639 | 6/1991 | Hura et al. | |
| 5,326,542 | 7/1994 | Sizer et al. | 422/291 |
| 5,374,814 | 12/1994 | Kako et al. | 235/379 |

FOREIGN PATENT DOCUMENTS

| 47-45997 | 12/1972 | Japan |
| 49-24194 | 3/1974 | Japan |
| 62-42296 | 2/1987 | Japan |
| 58-124873 | 2/1988 | Japan |
| 63-47260 | 2/1988 | Japan |
| 63-66059 | 3/1988 | Japan |
| 63-112350 | 5/1988 | Japan |
| 63-92566 | 5/1988 | Japan |
| 3-209595 | 9/1991 | Japan |
| 4-114652 | 4/1992 | Japan |
| 58-124873 | 8/1993 | Japan |

OTHER PUBLICATIONS

Chemical Sterilization, edited by Paul M. Borick, Dowden, Hutchinson & Ross, Inc. 1973.
Analytical Proceedings, Jul. 1986, vol. 23, pp. 256–258.
M. Furuhashi, Principala Sterilization and Disinfection in Practice, pp. 40–51, 1976 (partial translation).

Primary Examiner—Nina Bhrat
Attorney, Agent, or Firm—Antonelli, Terry, Stout & Kraus, LLP

[57] ABSTRACT

A cash transaction machine includes a sterilizing unit for sterilizing bills by heat, a heating temperature of the sterilizing unit being detected by a sensor and maintained in a specified range, wherein a number of bills to be processed is limited because there is a possibility that if very many bills are processed by the sterilizing unit, the heat is absorbed by the bills and the heating temperature falls, and the germs are not killed effectively, wherein when the bills are not sterilized, the sterilizing unit is operated intermittently to thereby prolong its service life, and the bills are sterilized only when a specified transaction is selected, and wherein a pressure is applied to bills simultaneously with heating by the sterilizing unit to thereby remove folds and rumples of the bills.

42 Claims, 26 Drawing Sheets

CASH TRANSACTION MACHINE AND METHOD THEREFOR

CROSS-REFERENCE TO RELATED APPLICATION

The present application is a Continuation-In-Part of: (a) U.S. patent application Ser. No. 08/297,093 filed on Aug. 26, 1994 issued as U.S. Pat. No. 5,578,281; and (b) U.S. patent application Ser. No. 08/310,379 filed on Sep. 22, 1994 issued as U.S. Pat. No. 5,504,313 which is a division of U.S. patent application Ser. No. 07/637,785 filed on Jan. 7, 1991 issued as U.S. Pat. No. 5,374,814 on Dec. 20, 1994. The contents of above-mentioned patent applications are incorporated herein by reference.

A U.S. patent application Ser. No. 08/430,798 now allowed filed on the same date of the present application entitled CASH TRANSACTION MACHINE is a related patent application of the present application.

BACKGROUND OF THE INVENTION

This invention relates to a cash transaction machine for depositing and withdrawing by the user's manipulation, and more particularly to a cash transaction machine with a function to sterilize or disinfect bills.

A cash transaction machine having a function to sterilize bills is disclosed in JP-A-3-209595, in which sterilization methods by heat, ultraviolet rays, chemicals are revealed. In sterilizing bills by heat sterilization, a method of heating a bill with heating means provided on the transport path is effective. Heat sterilization of bills, such as this, is shown in JP-A-4-114652. In JP-A-4-114652, there is provided a heat sterilizing section, which includes a heating roller containing heating means such as a heater provided on the transport path, and a heat-resistant belt wrapping around the heating roller. Bills are moved between the heating roller and the heat-resistant belt as they transferred on the transport path, and the bills are heat-sterilized at the bill-holding section including the heating roller and the heat-resistant belt.

In a heat sterilization process in which the heating roller and the heat-resistant belt are raised to a high temperature and while a bill is passed between the heating roller and the heat-resistant belt, the bill is sterilized by heat, the temperature of the bill is at about room temperature at most before it comes in between the heating roller and the heat-resistant belt, and in order to raise the bill at this temperature to a sterilizable temperature while the bill is placed between the heating roller and the heat-resistant belt, a large quantity of heat is required. When bills are sterilized successively, the heating roller and the heat-resistant belt are deprived of a considerable quantity of heat in a short time, so that the temperature of the heating roller and the heat-resistant belt fall rapidly. Not only being deprived of heat by the bills, the heating roller and the heat-resistant belt themselves are radiating heat. Therefore, for heating the heating roller and the heat-resistant belt by the heating means during sterilization, it is necessary to provide a large capacity heat source to supply a quantity of heat equivalent to the deprived quantity of heat. However, it is difficult to install a large capacity heat source for reasons of power consumption, installation space, or the like. An important problem is how to maintain the heating roller and the heat-resistant belt at a sterilizing temperature.

By the examination of the germs on the circulating bills, the present inventors found that various kinds of germs, including *staphylococcus aureus* and *bacillus subtilis* adhere to the bills in circulation. Experimental research has been made into the heating condition for thermally killing the microbes including those mentioned above. To give an example, according to "Principal Sterilization and Disinfection in Practice—revised edition—" (issued by Nihon Iji Shimposha, Jul. 31, 1989), the sterilizing condition is 5 to 10 min at 60° C. for *staphylococcus aureus*, and 15 min at 104° C. for *bacillus subtilis*.

However, in a bill handling machine, when a bill heating section is provided along the transport path and bills are transferred and sterilized one after another, because this kind of machine transfers 7 to 12 bills in one second at the speed of about 1 m per second, even if the heating section is prolonged, the heating time that can be secured is 0.05 to 0.15 s at most, which does not satisfy the heating time as one of the sterilizing conditions mentioned above.

It is known that in the dying process of those germs, if the heating condition is fixed, the number of dead germs increases exponentially. As the heating time is reduced, the germicidal effect is decreased.

Therefore, in a bill handling machine, if a bill heating section is provided on the transport path and the bills which are transferred are sterilized one after another, when the heating time is so short as 0.05 to 0.15 s as mentioned above, by setting a higher heating temperature than in the above-mentioned literature, it is possible to obtain powerful germicidal effects. On the other hand, If the temperature of the heating roller and the belt is raised too high, problems deriving from the machine construction arise such as an increase in heat quantity produced, and danger of smoke generation and catching fire.

Meanwhile, in putting into practical application the sterilizing mechanism in the bill handling machine, it is not necessary to offer such a high germicidal effect as in sterilizing equipment used in medical scenes because a user touches a sterilized bill with his or her contaminated hand in daily life and not a few germs again adhere to the bill while it is stored in the purse. With this taken into consideration, the heating condition should be set.

SUMMARY OF THE INVENTION

An object of the present invention is to provide a bill sterilizing unit that can be mounted in an conventional automatic cash transaction machine and a cash transaction machine that can ensure an effective germicidal effects.

An automatic cash transaction machine according to the present invention comprises a receptacle for putting in and taking out bills, a bill storage box for storing bills, transporting means for transporting bills between the receptacle and the bill storage box, sterilizing means for transferring bills to and from the transporting means and sterilizing the bills by heat, temperature detecting means for detecting the temperature of the sterilizing means, and control means for controlling the bill heating temperature of the sterilizing means so as to be in a specified temperature range in response to the temperature detected by the temperature detecting means and controlling transactions according to the temperature.

The present invention controls the sterilizing means under the condition that more than 90% of *staphylococcus aureus* adhering to bills is killed. In other words, the heating temperature and time by the sterilizing means are controlled so as to be 140° C. or higher and 0.05 to 0.15 s, respectively. The bills are heated while they are moving through the heating section, and more than 90% of *staphylococcus aureus* adhering to the bills are destroyed, which is sufficiently hygienic for daily life.

If the number of bills to be sterilized continuously is limited to a number at which the heating temperature does not fall below a specified temperature, it is possible to continuously sterilize less than a certain number of bills. By arranging for the number of bills that can be sterilized continuously to be more than the number of bills deposited or withdrawn in one transaction, bills can be sterilized securely without affecting transactions.

It is another object of the present invention to provide a cash transaction machine and a method which have money disinfection function.

It is another object of the present invention to impart good impression to users and a manager of a cash transaction machine by disinfecting moneys received and paid in the transaction in order to maintain the moneys in a good sanitary condition.

In order to achieve the above objects, the cash transaction machine for receiving and/or dispensing money by user's manipulation comprises: a receptacle for receiving and/or dispensing the money; a storage of the money; transport means for transporting the money between said receptacle and said storage; and disinfection means for disinfecting the money received and/or to be dispensed.

Further, the cash transaction machine of the present invention having disinfection means for heating money during transport to disinfect the money, the disinfection means comprises first transport means including heat means for heating money, for transporting the money, and second transport means including an endless belt and facing said first transport means for holding the money therebetween to transport the money.

The cash transaction method of the present invention comprises the steps of: receiving money from a receptacle; transporting the money by a transport unit; disinfecting the money by a disinfection unit arranged in said transport unit during the transportation of the money; storing the transported money in a storage; and dispensing money from a discharge port by user's manipulation.

Further, the cash transaction method of the present invention comprises the steps of: receiving money from a receptacle; transporting the money by a transport unit; storing the transported money in a storage; disinfecting the money by a disinfection unit arranged in the storage; and dispensing the money from a discharge port by user's manipulation.

In the cash transaction machine of the present invention, the bills received from the receptacle are disinfected by the disinfection unit during the transportation by the transport unit or the store in the storage. In this manner, the bills dispensed from the cash transaction machine are kept in a better sanitary condition than that of the received bills.

In the cash transaction machine which transports the bills in the machine at a high speed, the disinfection unit includes first transport means having a heating unit built therein and second transport means including an endless belt. A wrap angle around which the first transport means and the second transport means contact is selected large so that a large contact angle is attained to heat the bills for a longer time.

DESCRIPTION OF THE PREFERRED EMBODIMENTS

Embodiments of the present invention will be described with reference to the accompanying drawings.

Figure 1:
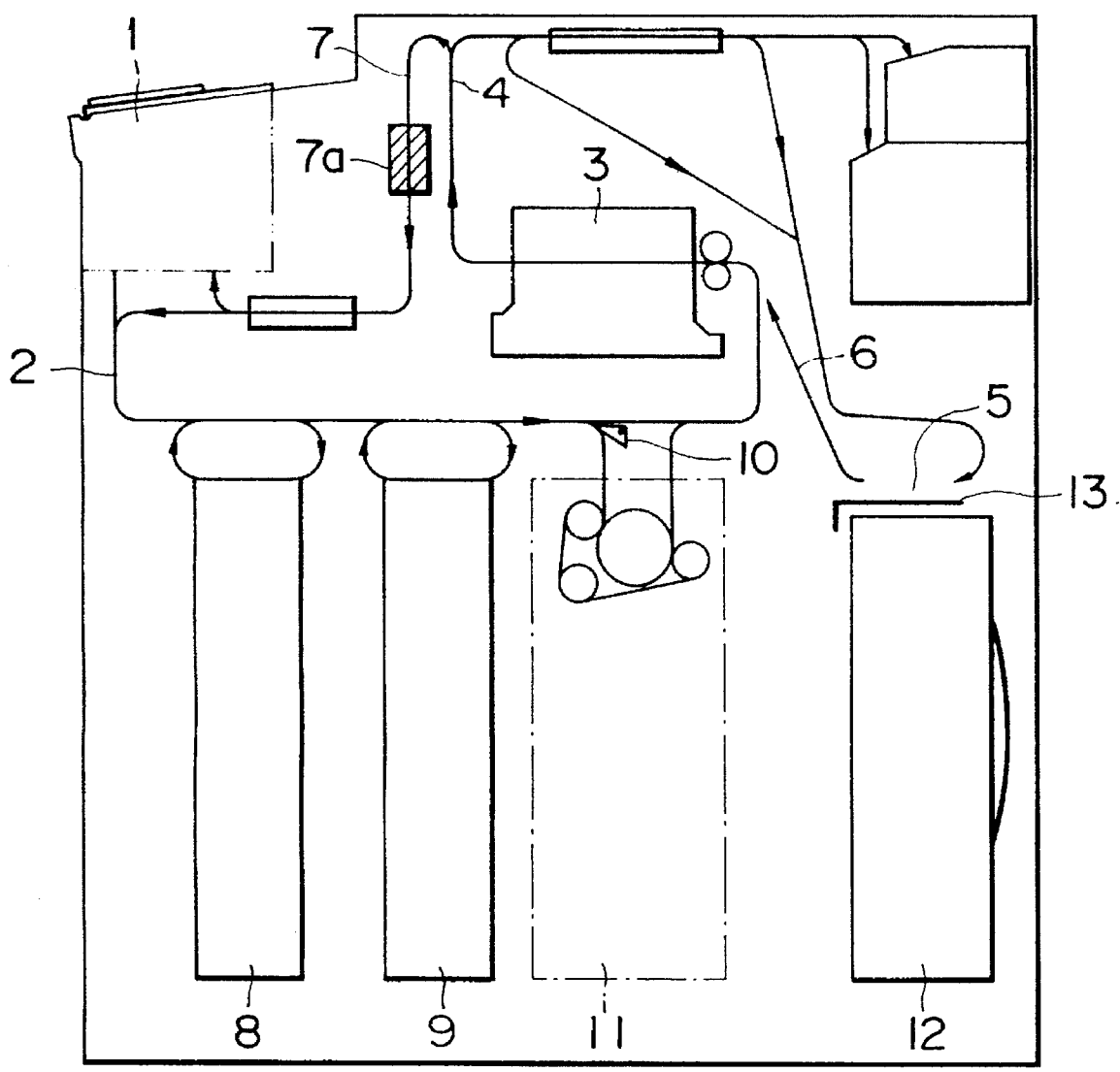
FIG. 1 is a diagram showing an embodiment of the present invention.

FIG. 1 shows a cash transaction machine as an embodiment of the present invention.

In a money receiving transaction, the user puts bills into a receptacle 1. The bills put in are separated from one another by a separating mechanism, not shown, in the receptacle 1, and are transferred on the transport path to a discriminator 3. The discriminator 3 discriminates the bills in terms of denomination, counterfeit or not, neat or damaged, and the number. The bills are further transferred through the transport path 4, and stacked in a temporary accumulation mechanism 5. If the transaction that the user performed is concluded, the bills are separated by a separating mechanism, not shown, transferred from the temporary accumulation mechanism 5 back to the discriminator 3 for discrimination, and passing through the transport paths 4, 7 and 2, sent to denomination boxes 8, 9 and stored classified by denomination, with which the money receiving transaction is finished. The denomination box 8 stores 1000-yen bills, and the denomination box 9 stores 10000-yen bills, for example.

In a money paying transaction, bills as many as the user requires from the denomination boxes 8, 9 are separated from one another by a separating mechanism, not shown, and sent onto the transport path 2. A gate 10 is installed on the midway of the transport path 2. In a money paying transaction, the gate 10 is switched to the side of the sterilizing/disinfecting unit 11, and the bills are transferred to the sterilizing/disinfecting unit 11 where they are sterilized or disinfected. After sterilized or disinfected by the sterilizing/disinfecting unit 11, the bills are passed through the transport paths 2, 4 and 7, stacked in the receptacle 1 and dispensed, with which the money paying transaction is finished. The sterilizing/disinfecting unit 11 carries on heat sterilization, which will be described later, and the bills stacked in the receptacle 1 may sometimes be hot. Therefore, a bill cooling unit 7a may be installed on the transport path 7 to cool the bills heat-sterilized by the sterilizing/disinfecting unit 11 so as not to give the user a feeling of discomfort. Since there is provided a part of the transport path to detour the sterilizing/disinfecting unit 11, so that by switching over the gate 10, the sterilizing/disinfecting unit 11 can be detoured.

When the bills in the denomination boxes 8, 9 are running short, the denomination boxes 8, 9 are replenished with bills from a bill cassette 12. In other words, since the bill cassette 12 is detachable, a clerk in charge sets bills in the bill cassette 12. After the separator 13 is withdrawn, the bills are sent out of the cassette 12 by a separating mechanism, not shown, and are sent through the transport path 6 to the discriminator 3, which discriminates the bills of different denominations and counts the bills. Then, the bills of different denominations are separately replenished or filled in the respective denomination boxes. The temporary accumulation mechanism 5, the bill cassette 12, and the separator 13 may be constructed as shown in JP-A-62-42296, for example.

When either of the denomination boxes 8, 9 becomes full, the bills are sent out of the full denomination box 8 or 9, and after the discriminator 3 finishes the discrimination and counting of the bills of different denominations, the bills are brought back in the cassette 12. Or, all bills may be recovered from the denomination boxes 8, 9 and counted by the discriminator 3 to carefully examine the quantity of bills present in the machine. Moreover, by moving the bills sequentially through the discriminator 3 when they are sent to the denomination boxes 8, 9 or the bill cassette 12, the quantity of bills present in the machine can be counted for careful examination. In the above recovery for examination, too, by switching the gate 10 of the transport path 2, the bills can be sterilized or disinfected.

Figure 6:
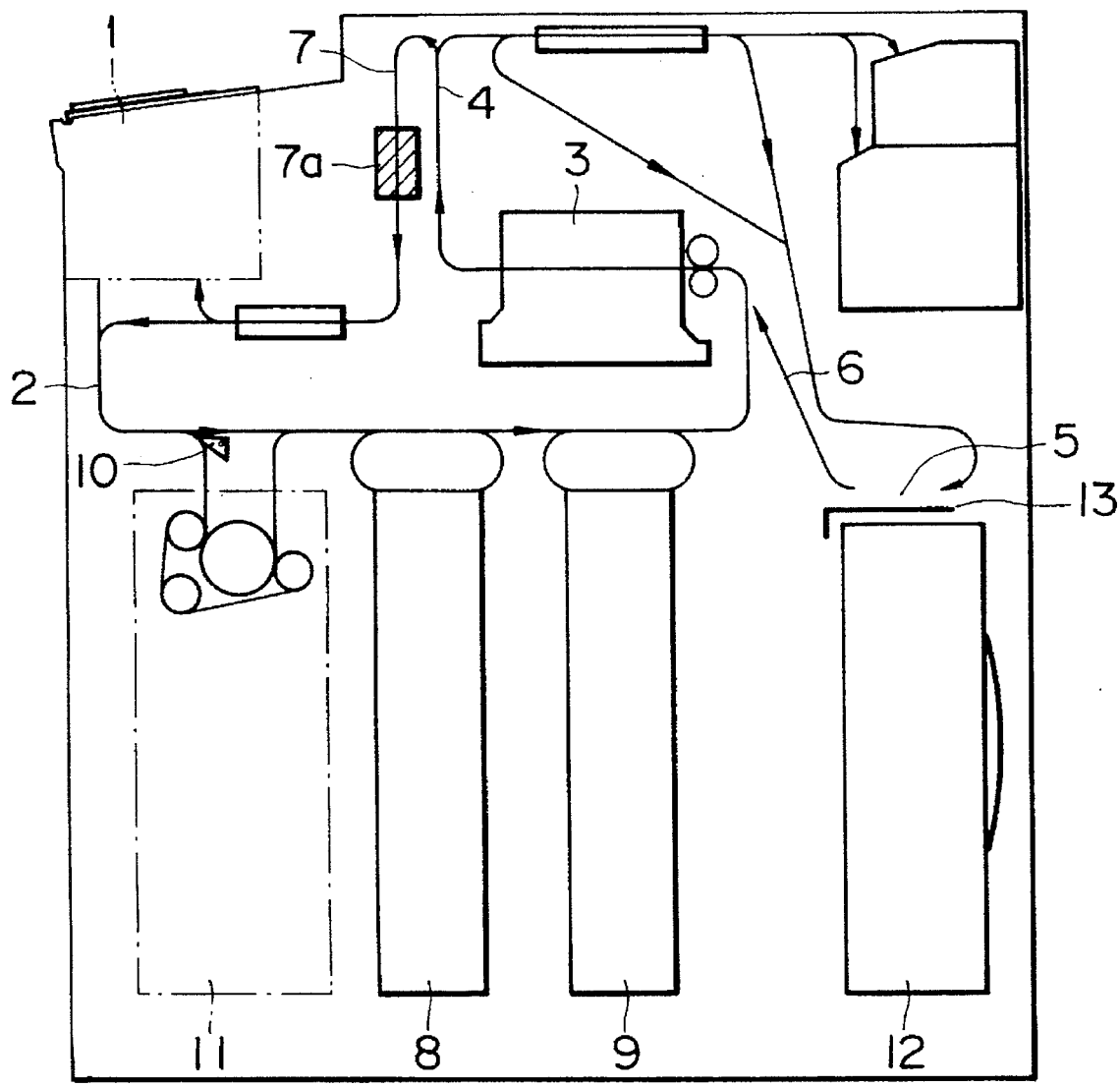
FIG. 6 is another embodiment of the present invention in which the sterilizing/disinfecting section is installed in the deposit route and the loading route.

FIG. 6 shows an embodiment in which the sterilizing/disinfecting unit 11 is provided on the upstream side of the denomination boxes 8, 9 on the transport path 2. In the construction in FIG. 6, the bills can be sterilized or disinfected in the money receiving transaction, or bill replenishing or loading operations. In the construction in FIG. 6, the sterilization or disinfection process is not performed in the money paying transaction.

The money receiving transaction includes a money counting process for accumulating bills that the user throws in the receptacle 1 into the temporary accumulation mechanism 5 and a received money receiving process for storing bills from the temporary accumulation mechanism 5 into the denomination boxes 8, 9. In the money counting process, the bills thrown in to the receptacle 1 are sent one after another onto the transport path 2, and after passing through the transport path 2, the discriminator 3 and the transport path 4, the bills are stacked in the temporary accumulation mechanism 5. The received money receiving process starts when as the result of the money counting process the transaction is concluded by obtaining the user's confirmation. The bills stacked in the temporary accumulation mechanism 5 are sent one after another onto the transport path 6, and passed through the discriminator 3, and the transport paths 4, 7 and 2. From the transport path 2, the bills are sent through the gate 10 to the sterilizing/disinfecting unit 11. After sterilized or disinfected, the bills are again sent to the transport path 2, and stored in the denomination boxes 8, 9 provided on the downstream side of the transport path 2.

Figure 2:
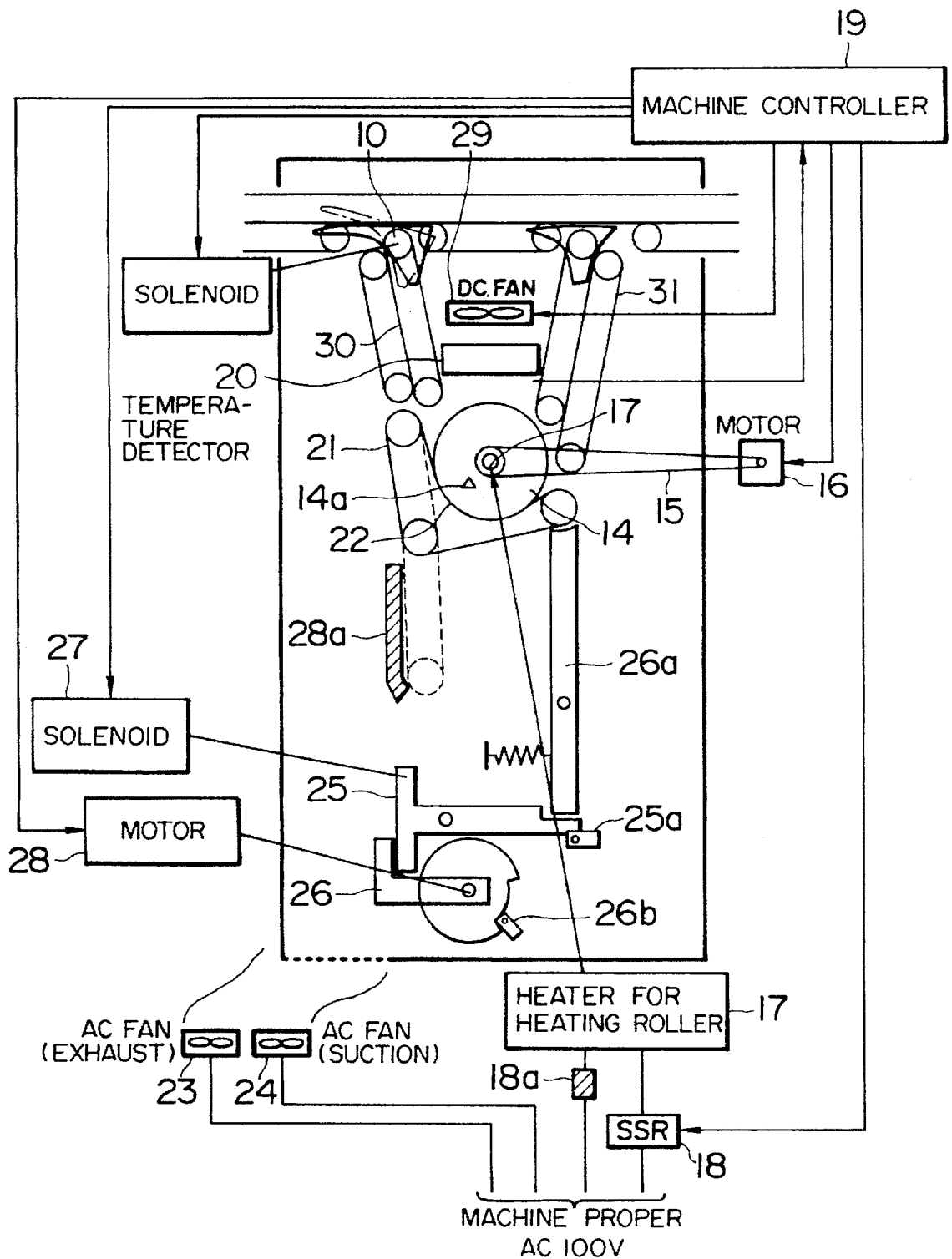
FIG. 2 is a diagram showing the construction of a sterilizing/disinfecting section for sterilization or disinfection.
Figure 3:
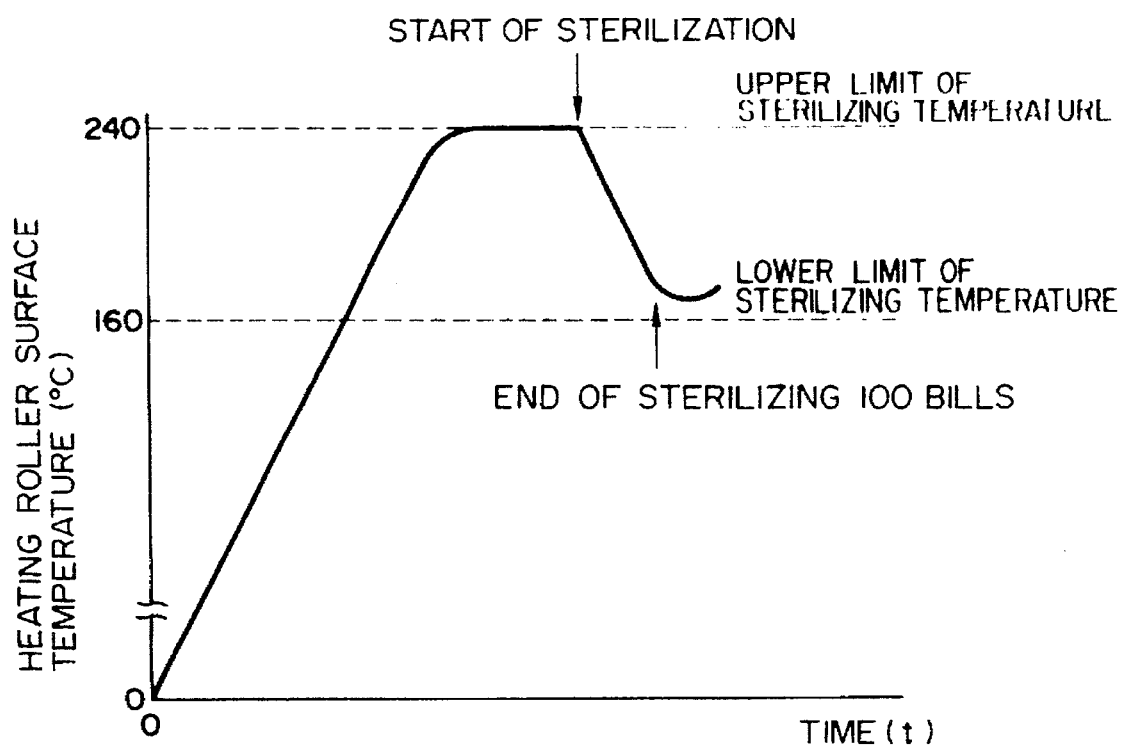
FIG. 3 is a diagram showing temperature changes of the sterilizing section.

With reference to FIG. 2, description will be made of the sterilizing/disinfecting unit 11 in the cash transaction machine shown in FIGS. 1 and 6. FIG. 2 shows the construction of the bill sterilizing/disinfecting unit 11.

Reference numeral 14 denotes a metal heating roller for heat sterilizing the bills, which is supported by a bearing, not shown, and is connected to a heating roller driving motor 16 by a timing belt so as to be rotated by the motor 16. The heating roller driving motor 16 is a stepping motor variable in the rotating direction and the rotating speed. A sensor 14a detects whether or not the heating roller 14 is rotating. When the power source is turned ON, the heating roller 14 should be rotated, but if the heating roller does not rotate, preventive measures against heat are taken as described later, and for this reason, the sensor 14a detects whether or not the heating roller 14 is rotating.

Reference numeral 17 denotes an electric heater to heat the heating roller 14, and the electric heater 17 produces a quantity of heat to keep the surface temperature of the heating roller 14 at the sterilizing temperature or higher. For convenience of depiction, the electric heater 17 is drawn separately from the heating roller 14, but in actuality, the electric heater 17 is mounted close to the shaft of the heating roller. A switch 18 for controlling the supply of electric power is attached to the line for supplying the heater with electric power, so that the electric heater 17 can be turned ON and OFF by the controller 19. A thermal protector 18a serves as a fuse when the electric heater 17 cannot be turned OFF owing to a fault of the switch 18 even though the electric heater 17 is raised to a specified temperature or higher.

Reference numeral 20 denotes a temperature detector to measure the surface temperature of the surface temperature of the heating roller 14, and the measured temperature is input to the controller 19. The controller 19, according to temperature data supplied by the temperature detector 20, controls the switch 18 to manage the surface temperature of the heating roller 14.

Reference numeral 21 denotes a heat-resistant belt, which wraps around the heating roller 14, is under a necessary tension for sterilizing the bills, that is, a tension of 16 kgf or over. The section 22 where the heat-resistant belt 21 and the heating roller 14 are in contact with each other is the bill heating section. The bill heating section 22 is formed by arranging the heat-resistant belt 21 so as to feed bills by pressing the bill against the heating roller 14 for a certain angle or more. As the heating roller 14 and the heat-resistant belt 21 are rotated, the bills entered the heating section 22 are heat-sterilized while they are transferred.

Reference numerals 23, 24 denote exhaust and suction fans for preventing the ambient temperature of the sterilizing/disinfecting unit 11 from rising as it is heated by the heating roller 14.

Reference numerals 25, 26 denote locks for the heat-resistant belt 21 which are driven by a solenoid 27 and a gear motor 28, respectively. A sensor 25a senses if the lock 25 is open or closed. The lock 25 in the state shown in FIG. 2 is not covering the sensor 25a, so that the sensor 25a is sensing that the lock 25 is closed. A sensor 26b senses if the lock 26 is open or closed. The lock 26 in the state shown in FIG. 2 is not covering the sensor 26b, so that the sensor 26b is sensing that the lock 26 is closed. Reference numeral 29 denotes a fan to cool the heating roller 14 in an emergency.

In this embodiment, the time for heating a bill at the heating section 22 is 0.05 s and the required sterilizing temperature in this period of time is 160° C. to 240° C.

The surface temperature of the heating roller 14 and the heat-resistant belt 21 is raised by the electric heater 17 for sterilization, and the temperature necessary for sterilization is kept between 160° C. and 240° C., for example, by ON/OFF control of the heater 17.

In the bill sterilizing process, as bills pass through the heating section, the heat of the heating roller 14 and the heat-resistant belt 21 is taken away by the bills, and therefore their surface temperature decreases. To counteract this, some measures should be taken to ensure that the surface temperature of the heating roller 14 and the heat-resistant belt 21 does not fall below the lower limit of sterilizing temperature of 160° C., for example, even after all of the limit number of bills have passed continuously, if only the surface temperature of the heating roller 14 when the first bill passes through the sterilizing section has reached somewhere about 240° C., for example, even though the limit number of bills (100, for example) received or paid in one transaction have moved continuously. If the capacity of the electric heater 17 is increased, the number of bills that can be sterilized continuously will increase, indeed. However, to prevent the surface temperature of the heating roller 14 and the heat-resistant belt 21 from falling below the lower limit of sterilizing temperature when about 2000 continuously transferred bills, for example, are sterilized in loading or recovering bills, a very large electric heater is required, but such a heater will pose problems in terms of power consumption and difficulty in mounting.

With regard to the upper limit of sterilizing temperature, the higher the upper limit, the greater stress will be induced in the heating roller 14, the heat-resistant belt 21 and other materials of the sterilizing section. So, the upper limit of sterilizing temperature is set to be 240° C. obtainable by adding a minimum necessary temperature difference of 80° C., for example, for continuous sterilization, to the sterilization temperature lower limit of 160° C., for example, when the heating time is 0.05 s. The heat-resistant belt is under tension of 16 kgf or more necessary for bill sterilization.

A bill sterilizing process will be described briefly with reference to FIG. 4.

Since it takes time to heat the heating roller 14 and the heat-resistant belt 21 of the bill sterilizing section from room temperature to a specified sterilizing temperature, it is necessary to heat them somewhat in advance. After the power source to the cash transaction machine is turned ON (step 32), the electric heater 17 is turned ON (step 33) to set the heating roller 14 and the heat-resistant belt 21 to a temperature lower than the specified sterilizing temperature, in other words, to about 100° C., for example. The heating roller 14 and the heat-resistant belt 21 are in the standby state until they are heated to a preheating temperature (step 35). When the preheating temperature is reached, preheating temperature holding control is started to keep the surface temperature of the heating roller 14 and the heat-resistant belt 21 at a fixed temperature by turning the electric heater ON and OFF at somewhere about the preheating temperature (step 36). If the heat-resistant belt 21 is kept stationary during the above-mentioned standby state for preheating, there is a possibility that heat is applied only to a part of the heat-resistant belt 21 and that part is damaged. Therefore, it is desirable that the heating roller 14 and the heat-resistant belt 21 should be kept rotating at all times when they are on stand-by. To this end, after the electric heater is turned ON (step 33), the heating roller 14 and the heat-resistant belt 21 are kept rotating at low speed (step 34). At this point in time, the heating roller 14 is rotated only to prevent the heat-resistant belt 21 from being damaged, so that the heating roller 14 has only to be driven at lower speed than normally. While the heating roller 14 and the heat-resistant belt 21 are rotating, it is necessary to make sure that they are rotating without fail. If they are not rotating, this should be regarded as abnormal, and the electric heater 17 need to be turned OFF to prevent damage to the heat-resistant belt 21 in out-of-step condition. While this preheating temperature holding control is being implemented, the transport paths outside the heating roller 14 and the heat-resistant belt 21 are at a standstill.

The sterilizing section waits under this condition for a transaction involving bill sterilization to start (step 37). When a transaction involving bill sterilization, say, a money paying transaction is selected, the heating roller 14 and the heat-resistant belt 21 are heated to a sterilizing temperature, and the driving speed of the heating roller 14 is accelerated to a bill-transferable speed to implement sterilizing transfer control for sterilizing the bills (step 38). When the sterilizing transfer control (step 38) is finished, the preheating temperature holding control is started again to decrease the surface temperature of the heating roller 14 and the heat-resistant belt 21 and keep them at the preheating temperature (step 39), and the machine waits for a transaction involving bill sterilization to start (step 37). If a transaction without bill sterilization is selected, the heating roller 14 and the heat-resistant belt 21 are rotated at low speed and the surface temperature is at the preheating temperature.

Figure 5:
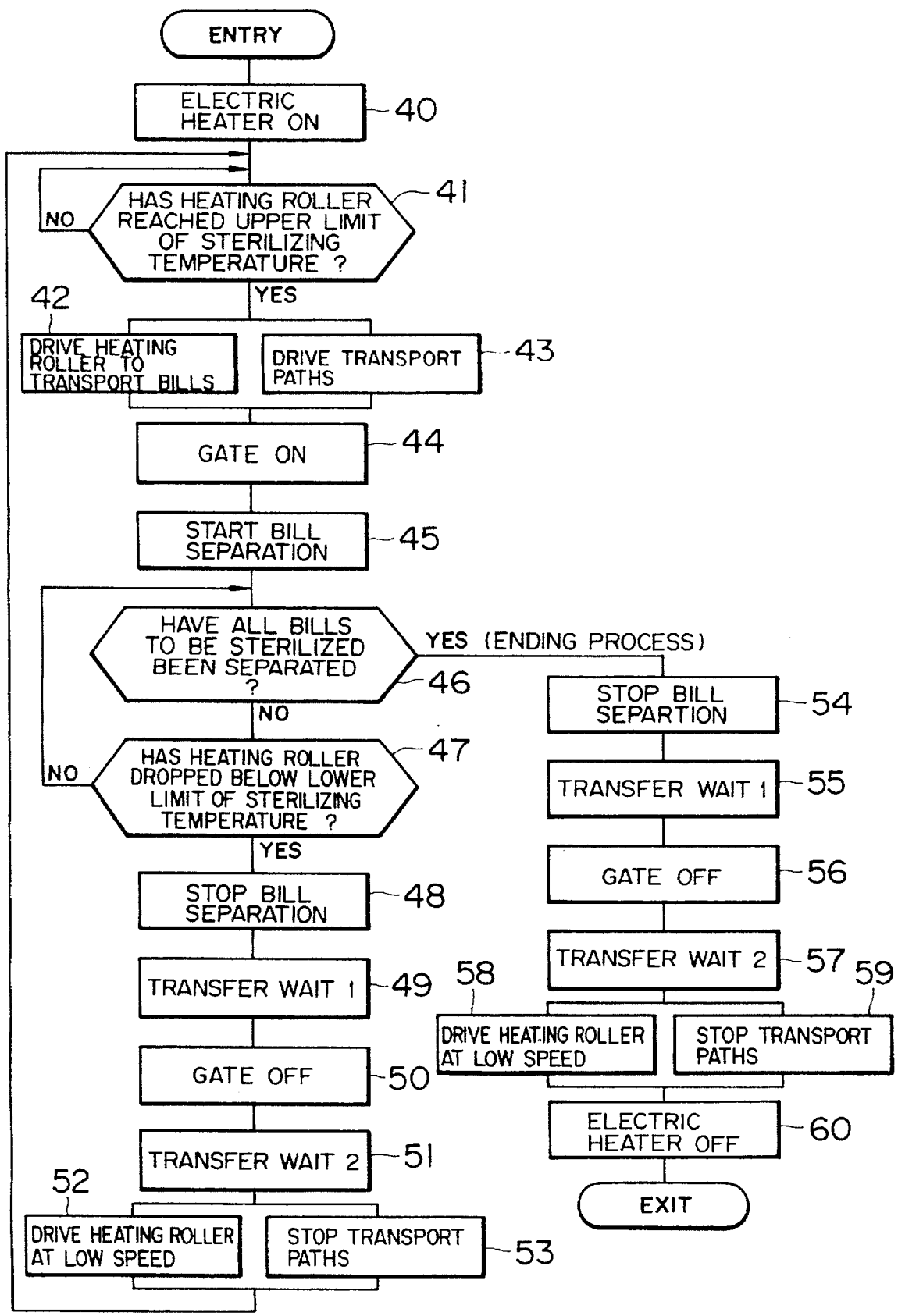
FIG. 5 is a detailed flowchart of sterilizing transport control.

Details of the above-mentioned sterilizing transfer control (step 38) will be described with reference to the flowchart in FIG. 5.

When a transaction involving bill sterilization is selected, in order that the heating roller 14 and the heat-resistant belt 21 which have been held at the preheating temperature should be raised to the sterilizing temperature, the electric heater 17 is turned ON (step 40), and the machine waits for the heating roller 14 and the heat-resistant belt 21 to reach the upper limit of sterilizing temperature (step 41). When they reach the upper limit of sterilizing temperature, the heating roller 14 and the heat-resistant belt 21 are in the state capable of sterilizing the bills. Therefore, the rotating speed of the heating roller 14 is increased to assume the bill-transferable state (step 42). At the same time, the bill transport paths 2, 4, 6, and 7 shown in FIG. 1 are driven (step 43). At this time, the heating roller 14 and the heat-resistant belt 21 are already at the upper limit of sterilizing temperature. An apparently rightful way of thinking would be that the electric heater 17 should be turned OFF, and when the heating roller 14 and the heat-resistant belt 21 fall to the lower limit of sterilizing temperature, the electric heater 17 should be turned ON. However, it is probable that when the bills are passed through the sterilizing section, the heating roller 14 and the heat-resistant belt 21 are deprived of a large quantity of heat by the passing bills, and their temperature may fall considerably. For this reason, the electric heater 17 is left in the ON condition. Some arrangement should be made so that the electric heater 17 is turned OFF if the upper limit of sterilizing temperature is exceeded. Under this condition, the gate 10 is turned ON (step 44), and a separating mechanism, not shown, of the denomination box 8 or 9 is driven to separate the bills (step 45). The bills which have been separated from one another by the separating mechanism are sent onto the transport path 2 one after another at fixed intervals, and are transferred to the bill sterilizing unit 11. The bills transferred on the transport path 2 are switched to the sterilizing route by the gate 10 provided on the transport path 2, and are sent to the sterilizing unit 11. The bills are sent by the transport path 30 of the sterilizing unit 11 into the heating section 22 between the heating roller 14 and the heat-resistant belt 21. The bills which are held between the heating roller 14 heated to a temperature of 160° C. to 240° C., for example, and the heat-resistant belt 21 are heated and moved through the heating section 22 by the rotation of the heating roller 14 and the heat-resistant belt 21, and sent onto the transport path 31, brought back to the transport path 2, passed through the discriminator 3, transferred on the transport paths 4, 7, put into the receptacle 1, and drawn out by the user.

By the above operations, the bills are separated and sterilized one after another, and when a specified number of bills have been separated, the ending process is performed (step 46), and for this while, the temperature of the heating roller is monitored to see if it decreases below the lower limit of sterilizing temperature (step 47). In case the selected transaction is a money paying transaction of 100 bills or less, the heating roller does not fall below the lower limit of sterilizing temperature, so that the process proceeds from step 46 to the ending process, the separating operation is stopped (step 54), and the machine waits for the finally separated bill to arrive at the sterilizing unit (step 55), and when the bill arrives, turns the gate 10 OFF (step 56). The machine waits for the last bill to pass the sterilizing unit and arrive at the receptacle 1 shown in FIG. 1 (step 57), and when the last bill arrives, stops the transport paths 2, 4, 6 and 7 (step 59). Moreover, the heating roller 14 is switched to the low-speed drive (step 58), the electric heater 17 is turned OFF (step 60), thereby reducing the temperature of the heating roller 14 and the heat-resistant belt 21. After the above operations are finished, the preheating temperature holding control shown in the flowchart in FIG. 4 is started (step 39), with which the transaction is finished.

In the money paying transaction, the sterilizing unit operates such that the temperature of the heating roller 14 and the heat-resistant belt 21 does not decrease below the lower limit of sterilizing temperature. However, in a recovery transaction or the like, when more than a certain number of bills are passed continuously through the sterilizing section between the heating roller 14 and the heat-resistant belt 21, the sterilizing section sometimes goes down below the lower limit of sterilizing temperature. Therefore, when at step 47 the heating roller goes down below the lower limit of sterilizing temperature during the sterilizing process, the separating operation by the separator is stopped temporarily (step 48), and the machine waits for the finally separated bill to arrive at the sterilizing unit (step 49), and when the bill arrives, turns the gate 10 OFF (step 50), and waits for the final bill to pass through the sterilizing unit and to be stored in the cassette 12 (step 51), and when the bill is stored, stops the transport paths 2, 4, 6 and 7 (step 53). At the same time, the heating roller 14 is switched to the low-speed drive (step 52), and the bill sterilizing process is terminated. Under this condition, the electric heater 17 stays ON, the machine waits for the heating roller 14 and the heat-resistant belt 21 to be restored to the upper limit of sterilizing temperature (step 41), and when the upper limit is reached, the bill sterilizing process is started. When the sterilizing process has been done for all bills, the process moves from step 46 to the ending process. If there are a large number of bills to be sterilized, the above process is repeated.

In the above process, the separating operation is completely stopped. However, the temperature decrease of the heating roller 14 and the heat-resistant belt 21 can be prevented effectively by reducing the number of bills per unit time to be sent in between the heating roller 14 and the heat-resistant belt 21 by decreasing the separating speed, or not only by this decreasing the separating speed but also by decreasing the transfer speed of the transport path 2 and the rotating speed of the heating roller 14.

Figure 4:
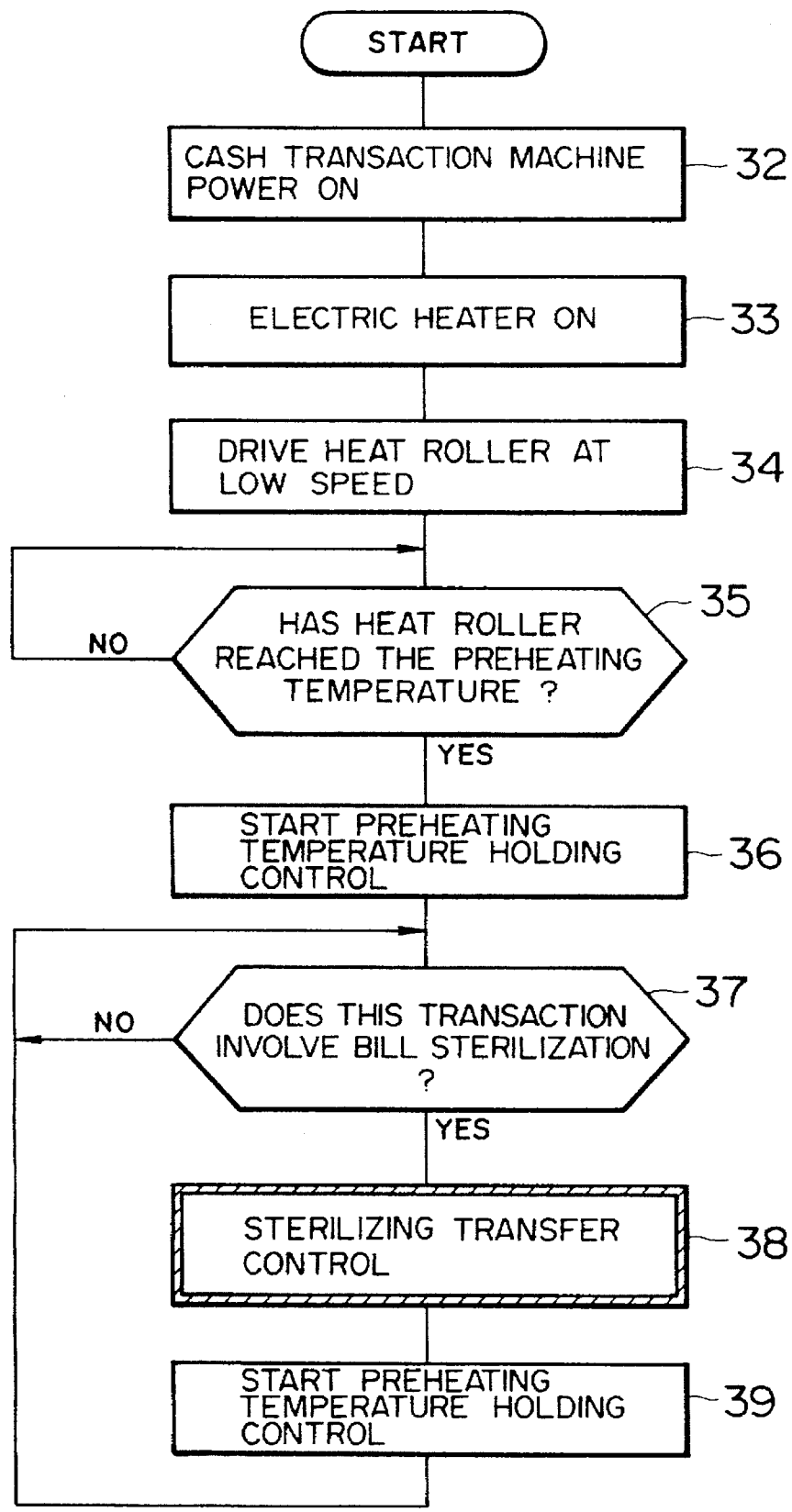
FIG. 4 is a flowchart of operation control in sterilizing bills.

In the case of another embodiment shown in FIG. 6, the "received money receiving process in a money receiving transaction" at step 37 in FIG. 4 is performed as the "transaction involving bill sterilization" by the same control described above.

With reference to FIG. 2, description will now be made of a process to be executed when abnormality occurs in the sterilizing section during the sterilizing process. When bills are left untransported in the heating section 22, if the bills are in contact with the heating roller 14 for a long time, the bills may be damaged. When the bills are left untransported, the power source to the lock solenoid 27 is turned OFF, the lock 25 is released, causing the heat-resistant belt 21 to be disengaged, so that the bills stuck in the heating section 22 are released. When the lock 25 of the heat-resistant belt 21 is released, the fan 29 installed above the heating roller 14 is rotated to quickly cool the heating roller 14 as an emergency step. Another effect of rotating the fan 29 is to blow off the bills left untransported in and around the heating section 22. The heat-resistant belt 21, which in the open state, is so designed as to be restored to the initial state by being automatically placed in the locked condition. Details of opening/closing control of the heat-resistant belt 21 will be described with reference to FIG. 7.

The lock mechanism is normally in the standby mode, the lock 25 is fixed by the lock stopper 26, and the lock lever 26a used to support the heat-resistant belt 21 is held by the lock 25 while the lock lever 26a is in a condition supporting the heat-resistant belt 21. (standby mode)

When a money paying transaction is started, the lock solenoid 27 is turned ON to hold the lock 25, and at the same time, the lock stopper 26 is moved to the open position by the stopper motor. As a result, the lock 25 is placed in the closed or open condition according to ON/OFF condition of the lock solenoid 27. (operation mode)

Under this condition, when abnormality occurs, the lock solenoid 27 is turned OFF, thus placing the lock 25 in the open condition. Accordingly, the lock lever 26a is disengaged, and the heat-resistant belt 21 is opened. (open condition)

Under this condition, the heating roller 14 and the heat-resistant belt 21 continue to rotate for a specified amount and stops after all bills sent by the gate 10 into the sterilizing section are released.

The closing process takes place as follows. When the transport paths are stopped, the remaining bills are removed, and then the heat-resistant belt 21 is closed. (closing process)

When the lock stopper motor 28 is rotated for a specified amount, a lifting bracket 28a turns to move the heat-resistant belt 21 to the closed position, and the lock lever 26a moves to a position where the lock lever supports the heat-resistant belt 21. Under this condition, the lock solenoid 27 is turned ON, so that the lock 25 locks the lock lever 26a. Under this condition, the stopper motor 28 is rotated in reverse direction, thus placing the lock stopper in the closed position to fix the lock 25. Even if under this condition the lock solenoid 27 is turned OFF, the lock 25 is supported by the lock stopper 26. Thus, the lock mechanism is in the standby mode. (standby mode)

Figure 8:
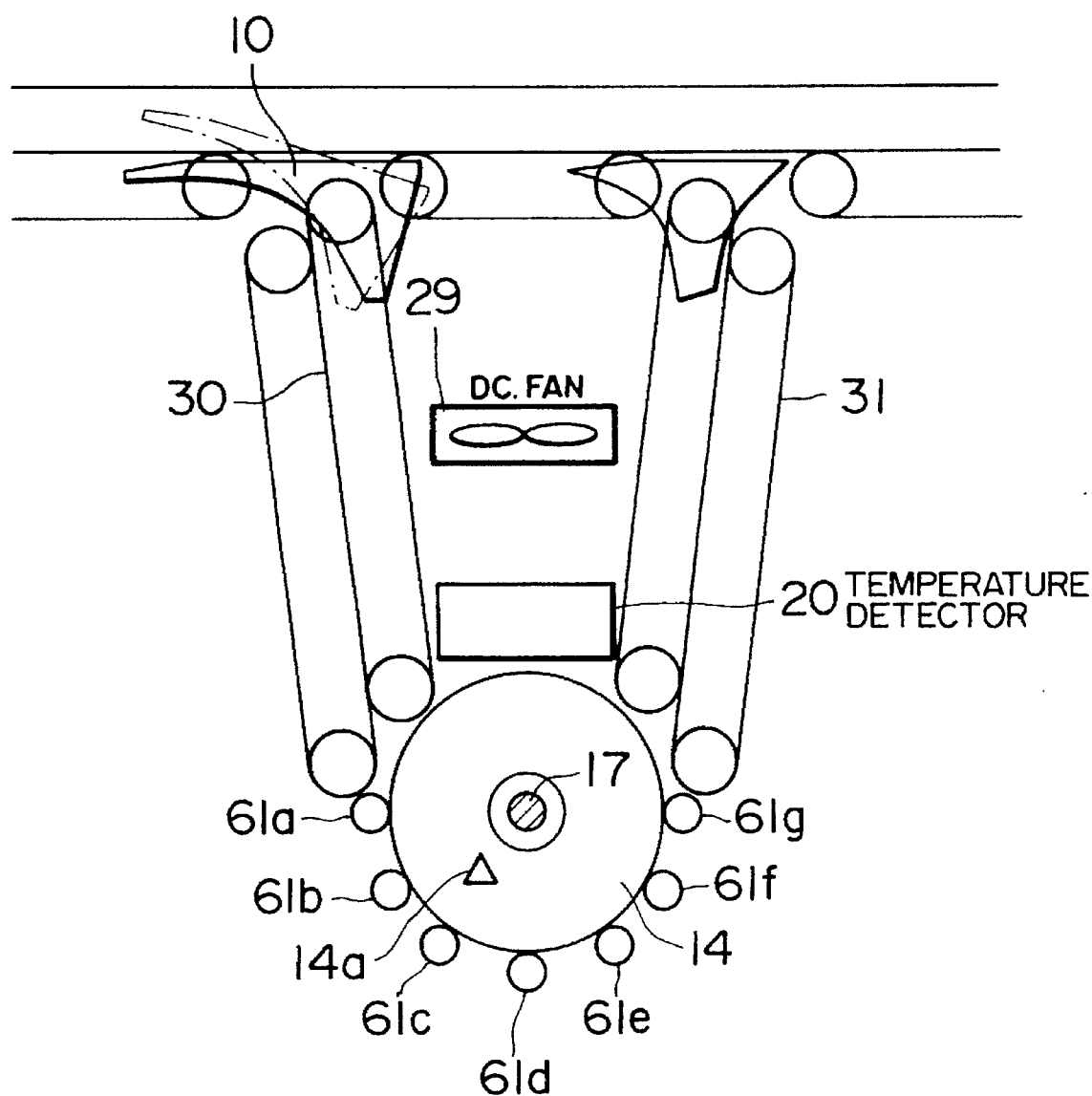
FIG. 8 is a diagram showing an illustrative embodiment of the heat sterilizing section.

In the above description, the sterilizing/disinfecting unit for sterilizing the bills is formed by the heating roller 14 and a heat-resistant belt 21 disposed as if to surround the heating roller 14, as shown in FIG. 2. If the sterilizing/disinfecting unit is formed by the heating roller 14 and a plurality of rollers 61a to 61g placed against the circumference of the heating roller 14 as shown in FIG. 8, the bills passing through the heating section 22 sufficiently wrap around the heating roller 14 and are thereby heated, therefore, it is expected that the same effects can be obtained as in the sterilizing/disinfecting unit formed by the heating roller 14 and the heat-resistant belt 21. In other words, the bills are transported while they are pressed against the heating roller 14 for more than a certain angle or more.

Another embodiment of the present invention will next be described.

There are many germs adhering to the bills. In this embodiment, the kinds of germs to be killed are limited, and for this purpose, effective sterilizing conditions are set. Among the germs adhering to the bills, *staphylococcus aureus* causes food poisoning and is also drawing attention as a germ causing hospital infection, and therefore must be a target of sterilization. The germs with high pathogenicity, such as a coliform bacillus, which could be a direct cause of food poisoning, are equal to or weaker than *staphylococcus aureus* in resistance to heat. If sterilizing efforts are directed to *staphylococcus aureus*, the other germs can be killed. *Bacillus subtilis* is a germ having a character like an enzyme and is generally harmless, so that if the germ is excluded from the targets of sterilization, this will not pose any problem. For the reasons mentioned above, the targets of sterilization include *staphylococcus aureus* and other germs low in resistance to heat. With regard to the germicidal effect to the germs as the targets of sterilization, to reduce the germs to about one-tenth, in other words, the germicidal rate of about 90% is considered effective because this machine is used in everyday life and the germs to be killed adhere to the users' skin. According to the earlier-mentioned "Principal Sterilization and Disinfection in Practice—revised edition—", the heating time for killing 90% (reducing the number of germs to ¹⁄₁₀) by the sterilizing process is referred to as the D value (Decimal reduction value), and this is used as a common concept in sterilization.

Figure 9:
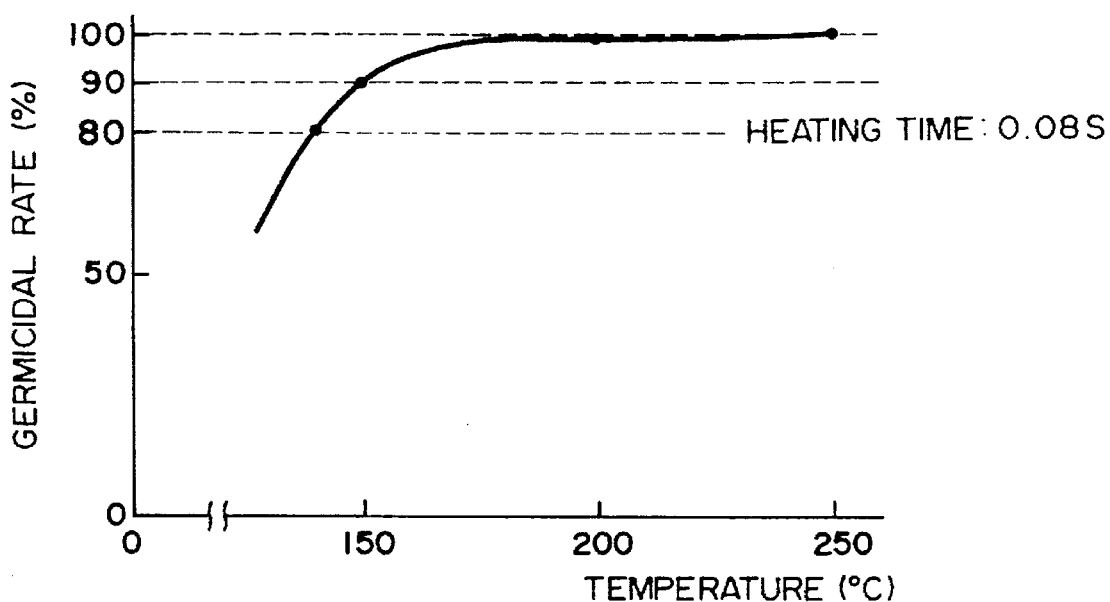
FIG. 9 is a diagram showing the relation between the heating temperature and the death rate for *staphylococcus aureus*.
Figure 10:
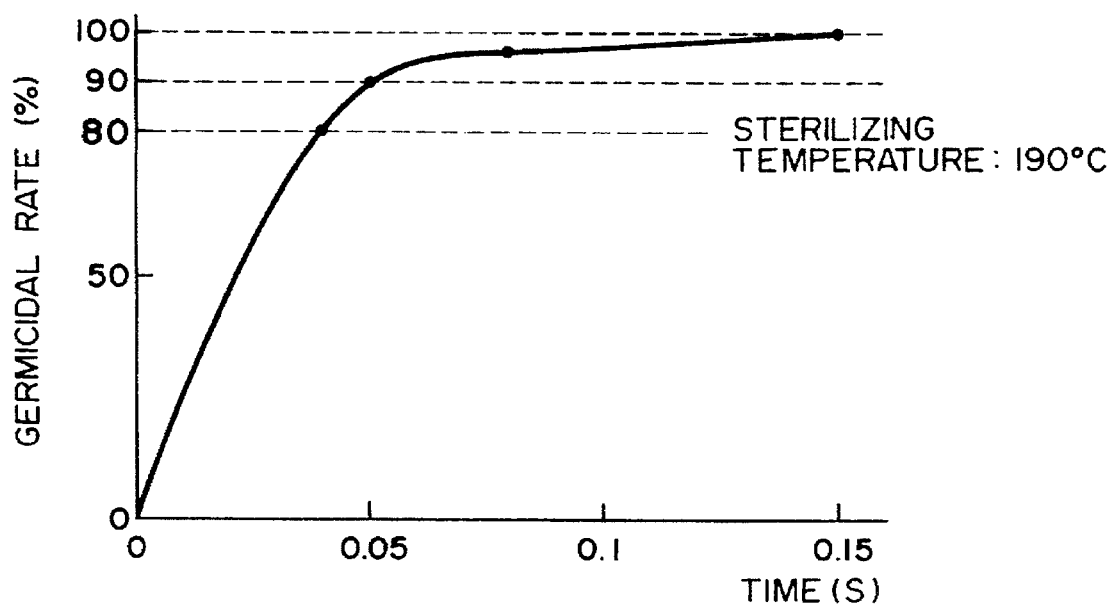
FIG. 10 is a diagram showing the relation between the heating time and the death rate for *staphylococcus aureus*.
Figure 11:
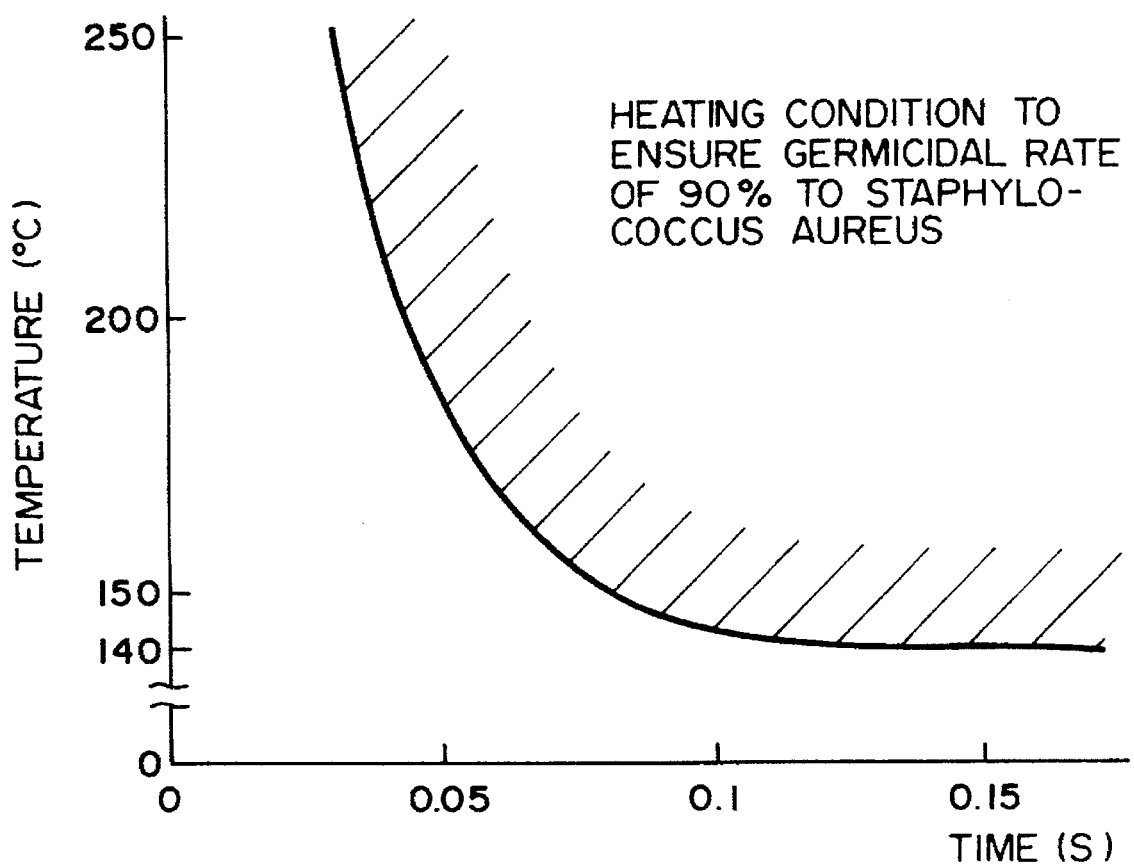
FIG. 11 is a diagram showing the germicidal effect by the relation between the heating time and the heating temperature for *staphylococcus aureus*.

The present inventors obtained experimental results as follows. The experimental results, shown in FIGS. 9 to 11, are the relations between the germicidal effects, and the heating time and heating temperature in the case of *staphylococcus aureus* when the bill sterilizing or disinfecting means comprises a rotating heating roller capable of heating the bills and a belt which, while being pressed against the heating roller, rotates in wrap-around contact with the heating roller. FIG. 9 shows the relation between the heating temperature and the germicidal rate when the heating time is 0.08 s and indicates that 90% of the germs can be killed at about 150° C. FIG. 10 shows the relation between the heating time and the germicidal rate when the heating temperature is 190° C. and indicates that 90% of the germs can be killed when the heating time is 0.05 s. FIG. 11 shows the heating condition which should satisfy the target value of 90% of the germicidal rate based on the experimental results using the heating time and temperature as parameters. From this, it has been clarified that to achieve about 90% of the germicidal rate to *staphylococcus aureus* as the target of sterilization when the heating time is about 0.15 s, the heating temperature need to be about 140° C. or above, and that in order to achieve about 90% of the germicidal rate when the heating time is 0.05 s, the heating temperature need to be about 185° C. or above.

Therefore, in a cash transaction machine, *staphylococcus aureus* and other germs weaker in resistance to heat than *staphylococcus aureus* are set as the targets of sterilization, the diameter and the rotating speed of the heating roller are set arbitrarily by controlling the heating roller surface temperature so as to be 140° C. or in a specified temperature range of 140° C. or above and by controlling the time of a bill being held between the heating roller and the heat-resistant belt wrapping around the heating roller so as to be in a range from 0.05 s or over to 0.15 s or less.

By dry air sterilization for heat-sterilizing the bills by the heating roller as mentioned above, the bills, while they are transferred, are heated to the heating temperature of 140° C. or above for a time corresponding to the D value of 0.05 to 0.15 s. The D value for reducing the germs to ¹⁄₁₀ can be made a value which is applicable to an ordinary cash transaction machine and suitable for the processing time and the transfer speed of an ordinary cash transaction machine, and can be secured without prolonging the processing time.

An embodiment which uses the above-mentioned condition will now be described. In this embodiment, the cash transaction machine is of the construction shown in FIG. 6, and the bill sterilizing unit 11 shown in FIG. 2 is used.

The heating roller 14 is an aluminum roller 60 mm in diameter, and its temperature is controlled so as to be about 185° to 190° C. at all times by the controller 19 according to information from the temperature detector 20. The heating roller 14 rotates at a speed of 6.5 revolutions/s. This heating roller speed is set so that the transfer speed of 1.2 m/s of the transfer mechanisms 2, 4 and 7 substantially coincides with the peripheral speed of the heating roller 14. The heat-resistant belt 21 wraps for about 180 degrees around the periphery of the heating roller 14, so that the bills transferred between the heating roller 14 and the heat-resistant belt 21 contact the heating roller 14 for about 0.08 s. In the above-mentioned embodiment, preheating temperature holding control at 100° C. is performed, but in this embodiment, the heating roller 14 and the heat-resistant belt 21 are controlled so as to be 180° to 190° C. at all times to be ready for a quick start of the sterilizing process.

Moreover, the machine in this case handles a maximum of 100 bills collectively, and processes the bills at a speed of 8 bills a second. The sterilizing/disinfecting unit 11 handles the bills at the same speed. In this process, if the quantity of received heat in the bills is greater than the quantity of heat supplied by the electric heater 17, the temperature of the heating roller 14 does not fall. In this embodiment, however, because of the restriction on the maximum power consumption, the temperature of the heating roller 14 was measured and found to be decreasing gradually, and after a continuous processing of a maximum of 100 bills, the heating roller 14 was found to have a temperature of about 150° C. by measurement. Therefore, when a maximum of 100 bills are processed continuously, the heating condition on the last bill for killing 90% of *staphylococcus aureus* as described with reference to FIG. 11 is satisfied sufficiently, and therefore the appropriate sterilizing effects can be obtained.

In order to increase the number of bills to be sterilized continuously to more than 100 in this embodiment, it is only necessary to further raise the initial setting temperature of the heating roller 14. However, because the heat resistance of the rubber or resin parts need to be increased, and also for reasons of technology and price, about 250° C. is considered to be the limit.

Figure 12A:
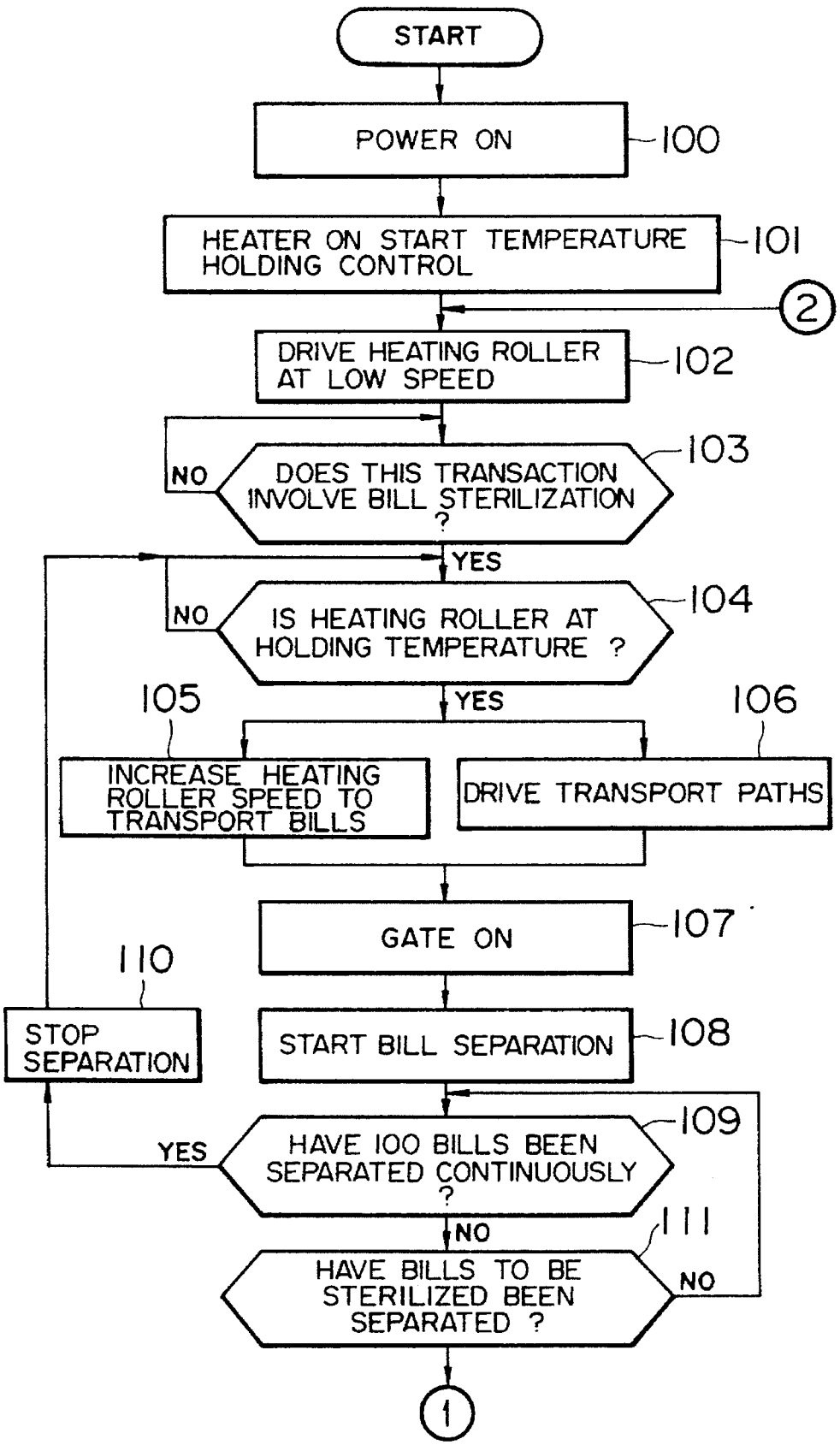
FIGS. 12A and 12B are flowcharts of operation control in the other embodiment of the resent invention.
Figure 12B:
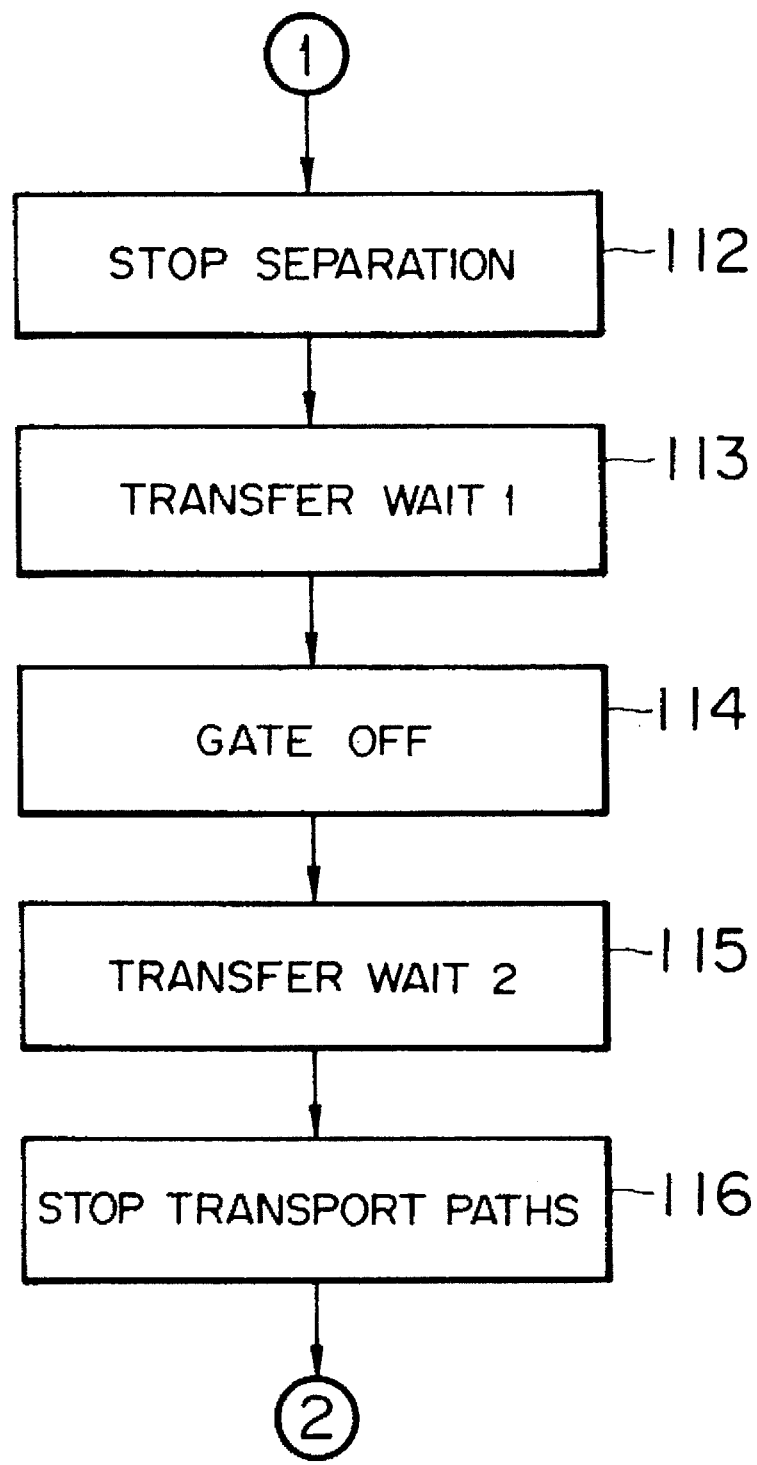

FIGS. 12A and 12B are flowcharts of operation control.

After power is applied to the cash transaction machine (step 100), the electric heater 17 is turned ON, and temperature holding control is started to hold the heating roller 14 and the heat-resistant belt 21 in a range of 185° to 190° C. (step 101). The heating roller 14 and the heat-resistant belt 21 are driven at low speed (step 102). The transport paths other than the heating roller 14 and the heat-resistant belt 21 are kept stationary.

The sterilizing unit is at the standby, waiting for a transaction involving bill sterilization to start (step 103). When a transaction involving bill sterilization, that is, a money receiving transaction, for example, is selected, a decision is made whether or not the heating roller 14 is at a holding temperature 185° to 190° C. (step 104). When the heating roller 14 is at the holding temperature of 185° to 190° C., the sterilizing unit is ready for the sterilization process, the rotating speed of the heating roller 14 is increased to make it possible to transport bills (step 105), and at the same time the bill transport paths 2, 4, 6 and 7 shown in FIG. 6 are driven (step 106). Under this condition, the gate 10 is turned ON (step 107), a separating mechanism, not shown, of the temporary accumulation mechanism 5 is driven to start the separation of bills (step 108). The bills separated by the separating mechanism are sent onto the transport path 6 one by one spaced at fixed intervals, and the bills are transferred through the discriminator 3, the transport paths 4, 7 and 2 to the bill sterilizing unit 11. The bills sent through the transport path 2 switched to the sterilizing route by the gate 10 provided on the transport path 2, and sent to the sterilizing unit 11. The bills are transferred on the transport path 30 of the sterilizing unit 11 into the heating section 22 between the heating roller 14 and the heat-resistant belt 21. The bills, which are placed between the heating roller 14 and the heat-resistant belt 21, are moved through the heating section 22 by the rotation of the heating roller 14 and the heat-resistant belt 21, and transferred onto the transport path 31, brought back to the transport path 2, and finally stored in the denomination box 8 or 9.

Since, by the above operations, the bills are separated and sterilized one after another, a decision is made whether or not 100 bills have been separated continuously (step 109). If 100 bills have been separated continuously, the separating operation is stopped temporarily (step 110), the temperature of the heating roller 14 is brought to 185° to 190° C. When all bills have been separated (step 111), the separating operation is stopped (step 112), the machine waits for the finally separated bill to arrive at the sterilizing unit (step 113), turns the gate 10 OFF (step 114), and waits for the last bill to pass through the sterilizing unit and to be stored in the denomination box (step 115), then stops the transport paths 2, 4, 6 and 7 (step 116).

The temperature range of 185° to 190° C. as the heating temperature condition adopted in this embodiment is about the same level as the heating temperature condition of the thermal fixing unit in a copier or laser beam printer of late. Therefore, if parts, such as a safety device against heat or fire, which have proven performance in terms of heat resistance, can be diverted to the cash transaction machine, this will greatly contribute to the improvement of reliability and the reduction of price of the machine.

In this embodiment, *staphylococcus aureus* and the germs with weaker resistance to heat are set as the targets of sterilization, and the diameter and the rotating speed of the heating roller is set so that the time of a bill being placed between the heating roller and the heat-resistant belt wrapping around the heating roller may be 0.08 s by controlling the surface temperature of the heating roller so as to be in a range of 185° to 190° C. in order that the germicidal rate of about 90% can be secured for a continuous processing of 100 bills transferred at a speed of 8 bills a second. Even after a continuous sterilizing process is performed, if the output of the electric heater is increased to prevent the surface temperature of the heating roller from falling, sufficient sterilizing effects can be obtained with the heating roller whose surface temperature is about 150° C.

When the diameter of the heating roller 14 is smaller than 60 mm in this embodiment, or when the transfer speed is faster than 1, 2 m/s in this embodiment, or when the wrapping angle of the heat-resistant belt 21 around the periphery of the heating roller 14 is smaller than about 180 degrees in this embodiment, the heating time can be shorter than 0.08 s in this embodiment. When a machine has a heating time of 0.05 s, for example, if the surface temperature of the heating roller is set to be 215° to 220° C., for example, the sterilizing effects same as in this embodiment can be obtained.

In this embodiment, the germs to be killed are *staphylococcus aureus* and other germs weaker in heat resistance than *staphylococcus aureus,* but if *bacillus subtilis* with higher heat resistance than *staphylococcus aureus* is included in the targets of sterilization, necessary and sufficient heating conditions can be set by examining the sterilizing effects by experiment like in the cases mentioned above.

In the above-mentioned embodiments, it is aimed to kill 90% or more order of *stapylococcus aureus* on a bill. However, a bill ordinary used is not subjected to sterilization and it is therefore noted that a sterilized bill, which is so sterilized that 80% or more order of *staphylococcus aureus* on the bill has been killed, is considered that it has been subjected to appropriate sterilization for ordinary use. In FIG. 9, it would be noted that 80% order of *staphylococcus aureus* was killed at a heating temperature of about 140° C. and a heating time of 0.08 seconds. In FIG. 10, it would be noted that 80% order of *staphylococcus aureus* was killed at a heating temperature of about 190° C. and a heating time of 0.04 seconds. Accordingly, a heating temperature of 140° C. or above and heating time of 0.04 to 0.15 realize sterilization by which 80% order of *staphylococcus aureus* adhering to the bill is killed.

Figure 13:
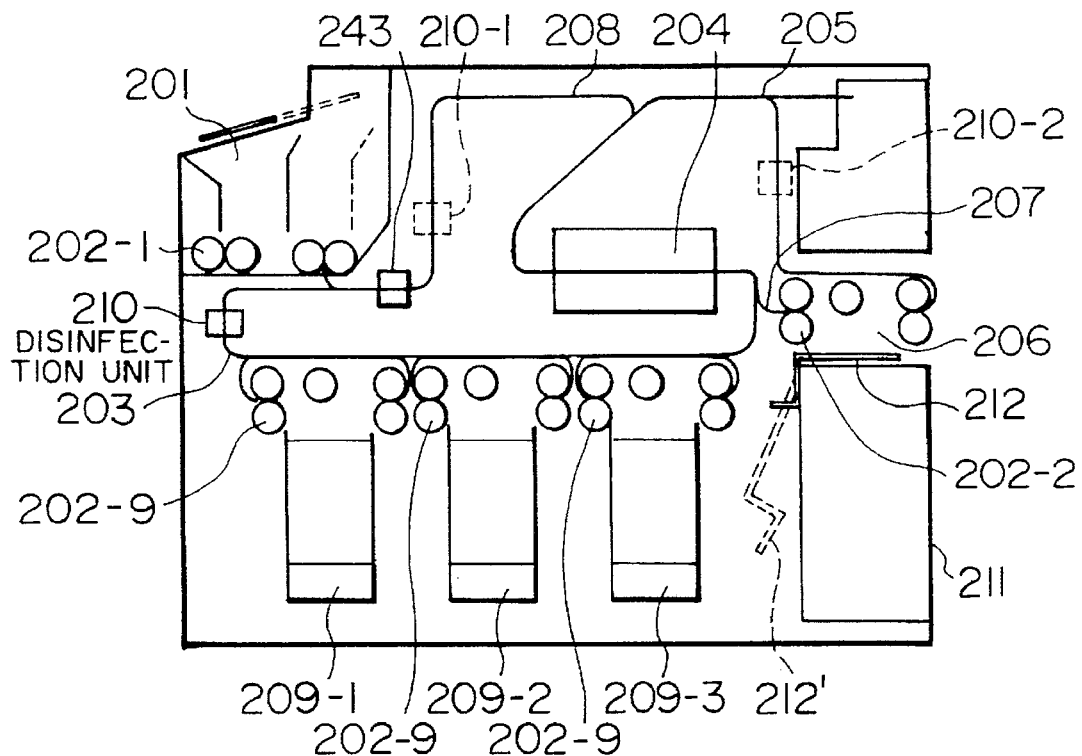
FIG. 13 shows a schematic view of an automatic teller machine in accordance with another embodiment of the present invention.

FIG. 13 shows an automatic teller machine in accordance with another embodiment of the present invention. The bills thrown in from a receptacle 201 are separated one by one by a separation unit 202-1 and they are transported to a discrimination unit 204 by a transport unit 203. The discrimination unit 204 discriminates the denomination, the genuineness, the damage and the number of sheets. They are further transported by a transport unit 205 and stored in a temporary store unit 206. If the transaction manipulated by a user is met the bills are separated by a separation unit 202-2, transported by a transport unit 207 to the discrimination unit 204 for discrimination, and transported to and stored in denomination boxes 209-1, 209-2 and 209-3 which store the bill by denomination, through transport units 208 and 203. This is the money receiving transaction.

In the money paying transaction, the required numbers of sheets of bills are separated from the denomination boxes 209-1, 209-2, 209-3 by a separation unit 202-9, they are stacked in the receptacle 201 and dispensed.

In the present embodiment of the automatic teller machine, the receptacle 201 is shared by a money receiving port and a money paying port, although a coin throw-in port and a charge port may be separated as they are in an automatic ticketing machine.

When the bills residing in the denomination boxes 209-1, 209-2 and 209-3 become small because the money paying transaction is larger than the money receiving transaction, bills are loaded in a removable/insertable bill cassette 211; a separator 212 is retracted to a broken line position 212', and the bills in the cassette 211 are removed by the temporary store unit 206. The bills are transported to the discrimination unit 204 through the transport unit 207; the discrimination unit 204 discriminates the denomination and the numbers of sheets of the bills, and the bills are stored in the denomination boxes 209-1, 209-2 and 209-3 through the transport units 208 and 203.

On the other hand, when the money receiving transaction is larger that the money paying transaction, and one of the denomination boxes 209-1, 209-2 and 209-3 become full; the bills are taken out of the full denomination box, discriminated by the discrimination unit 204 for denomination and the number of sheets, and stored into the cassette 211. All bills may be collected to check the balance of the bills in the machine. The balance of the bills in the machine may also be checked while they are sequentially transported into the denomination boxes 209-1, 209-2 and 209-3 and the bill cassette 211 through the discrimination unit 204.

In FIG. 13, a disinfection unit 210 is provided on the path of the transport unit 203. The disinfection unit 210 disinfects (including sterilization and pasteurization) the bills transported by the transport unit 203. FIGS. 14 to 22 show specific embodiments of the disinfection unit 210.

Figure 14:
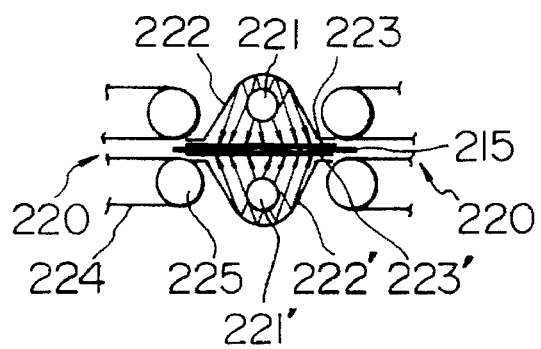
FIGS. 14 to 17 show schematic views of disinfecting devices which disinfects moneys during the transportation, in which FIG. 14 uses an ultraviolet ray, FIG. 15 uses a heated roller, FIG. 16 uses disinfecting liquid and FIG. 17 uses ozone as disinfection agent.

In FIG. 14, an electromagnetic wave irradiates the bills disintecting them. In the present embodiments, the disinfection unit (disinfection device) comprises a pair of ultraviolet ray lamps 221 and 221' arranged vertically relative to the transport unit in the path of the transport unit 220 which includes a belt 224 and a roller 225, reflection mirrors 222 and 222' arranged to cover the lamps 221 and 221', and guides 223 and 223' for holding the bills.

The ultraviolet rays from the lamps 221 and 221' irradiate both sides of the bill 215 transported one at a time by the transport unit 220 so that the bills are disinfected. A wavelength of the ultraviolet ray is selected to be most effective against the bacteria on the bills to be sterilized and disinfected.

While the ultraviolet ray is utilized in FIG. 14, other electromagnetic waves which have the disinfection function (including sterilization and pasteurization) such as microwave, X ray and ultrasonic wave may be employed. When the electromagnetic wave is harmful to the human body such as ultraviolet ray or X ray is used, the disinfection unit 210 is shielded.

Figure 15:
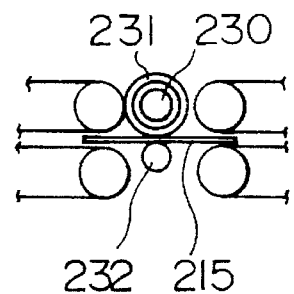

FIG. 15 shows an embodiment which heats the bill for the disinfection. In the present disinfection unit, the bill 215 is pressed to a heated roller 231 made of hard material such as metal having a heater 230 built therein, by a pressure roller 232 made of flexible material such as resin to disinfect (including sterilization and pasteurization) the bill. The heated roller is temperature-controlled by a temperature controller (not shown). The temperature of the heated roller is preferably high for the purpose of sterilization but is set below a burning temperature of the bill in order to prevent the deformation and burning of the bill. In the present embodiment, it is set to 220° to 240° C.

Figure 16:
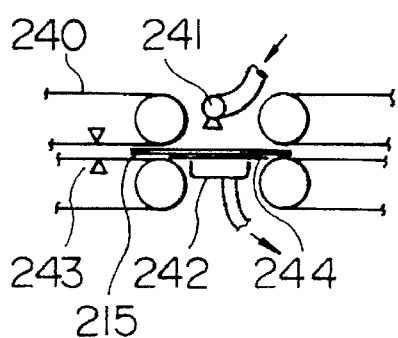

FIG. 16 shows an embodiment which disinfects the bill by drugs. The disinfection unit of the present embodiment comprises a money sensor 243 (to be described in detail later) mounted on the transport unit, a nozzle 241 connected to a drug supply source (not shown) for discharging the drugs, a drug recovery unit 242 and a guide 244 for holding the money. When the transport of the money is detected by the money sensor 243, the drugs are discharged to the money 215 from the nozzle 241 to disinfect the money. The drugs are recovered by the recovery unit 242 and returned to the supply source. The recovery unit is effective particularly when the drugs are harmful to the human body. It may be omitted when the drugs are not harmful to the human body.

Figure 17:
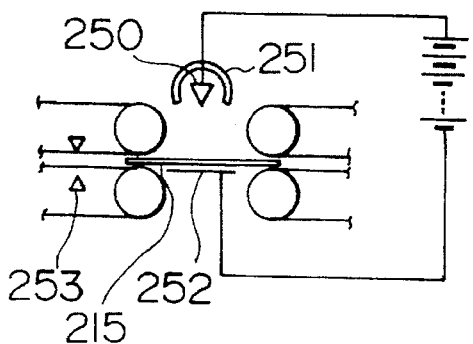

FIG. 17 shows an embodiment which disinfect the bill by ozone. The disinfection unit of the present embodiment comprises an electrode 250 connected to a positive pole, a cover 251 for the electrode 250 and a cathode 252 facing the electrode 250. A voltage is applied to the electrode 250 to generate ozone, and when the bill 215 is transported under the electrode, ozone is showered to disinfect the bill. This unit can be readily constructed.

FIGS. 18 to 22 show embodiments of the disinfection unit which can be suitably used in a cash transaction machine which transports bills in the machine at a high speed. In the automatic teller machine, 8 to 10 bills per second are received or dispensed. To this end, it is necessary to transport the bill at a velocity of 1 m/sec. In the embodiment of FIG. 15, if the bill is transported at such a velocity, the time which the bill contacts to the heated roller is short so that it is difficult to heat the bill to the required temperature and keep the bill at that temperature. The embodiments of the disinfection unit which attain a sufficient heating effect in such a machine are described below.

Figure 18:
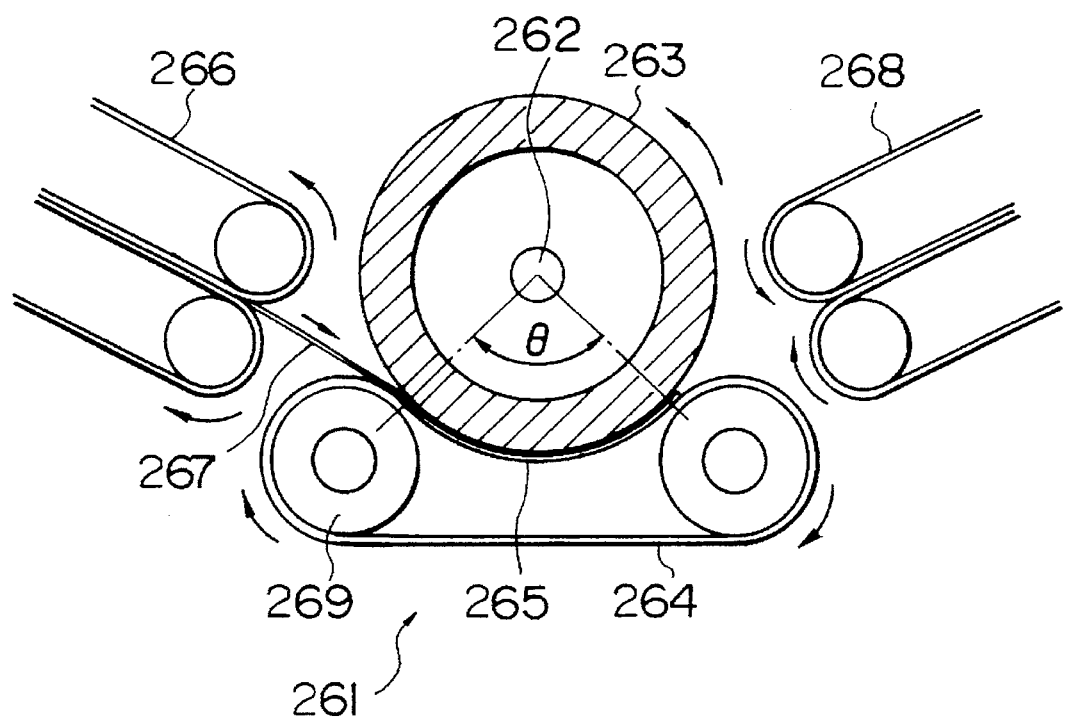
FIGS. 18 to 22 show schematic views of disinfecting devices which are used when moneys are transported at a high speed, in which FIG. 18 uses an endless belt to assure a long contact length, FIG. 19 uses a heater on an endless belt, FIG. 20 uses a pair of endless belts, FIG. 21 uses a water supply device and FIG. 22 uses an ultraviolet ray.

FIG. 18 shows an embodiment of a bill disinfection unit of the present invention.

The unit 261 of the present embodiment comprises a heated roller 263 including a metal roller having a halogen lamp 262 as heating means built therein and a rubber belt 264 supported by two pulleys 269. An appropriate tension is imparted to the rubber belt 264 so that it is pressed to the heated roller 263. It contacts to the heated roller 263 to wrap around it. A contact area of the heated roller 263 and the rubber belt 264 is a bill heating unit 265. The heated roller 263 and the rubber belt 264 rotate to transport the bill fed into the heating unit 265.

An operation of the present embodiment is described below.

The bill 267 fed to the disinfection unit 261 by the transport means 266 at the entry is fed into the contact area of the heated roller 263 and the rubber belt 264, that is, the heating unit 265. The bill 267 is held between the high temperature heated roller 263 and the rubber belt 264 and transported through the heating unit 265 by the rotation of the rubber belt 264 and the heated roller 263 while it is heated thereby, and discharged to the exit transport means 268 from the heating unit 265.

In the present embodiment, a wrap angle (θ) around which the heated roller 263 and the rubber belt 264 contact is selected large so that a large contact length, that is, a long contact time is assured and a large disinfection and sterilization effect is attained.

In the disinfection unit 261 of the present embodiment, the bill is disinfected and sterilized by heating and pressing the bill, and the folds and the rumples of the bill are removed. Further, the handling in the automatic cash transaction machine is easy.

Figure 19:
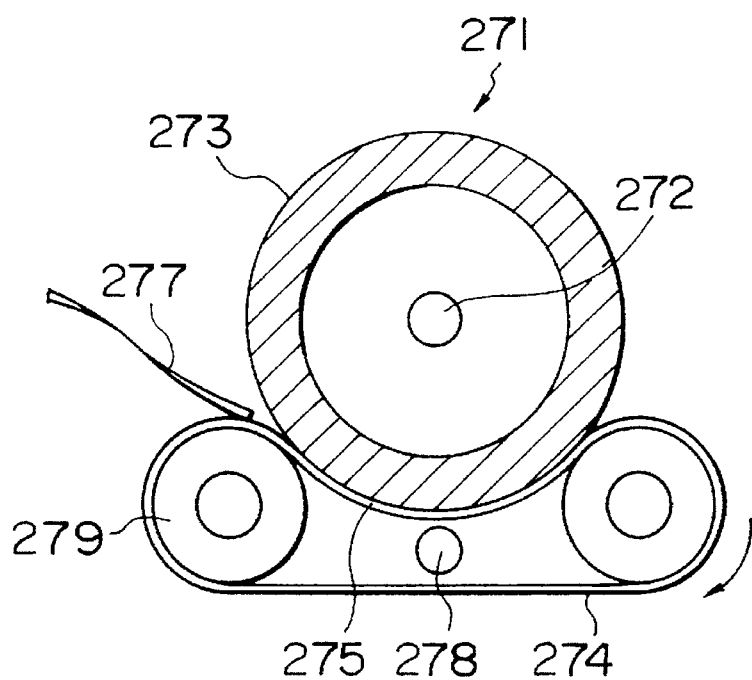

FIG. 19 shows other embodiment 271 of the present invention. In addition to the unit 261 of the embodiment of FIG. 18, a halogen lamp 278 is provided to face a pressure belt 274 as second heating means. In the unit 271 of the present embodiment, the bill 277 is heated in a shorter time so that a larger disinfection and sterilization effect is attained.

Figure 20:
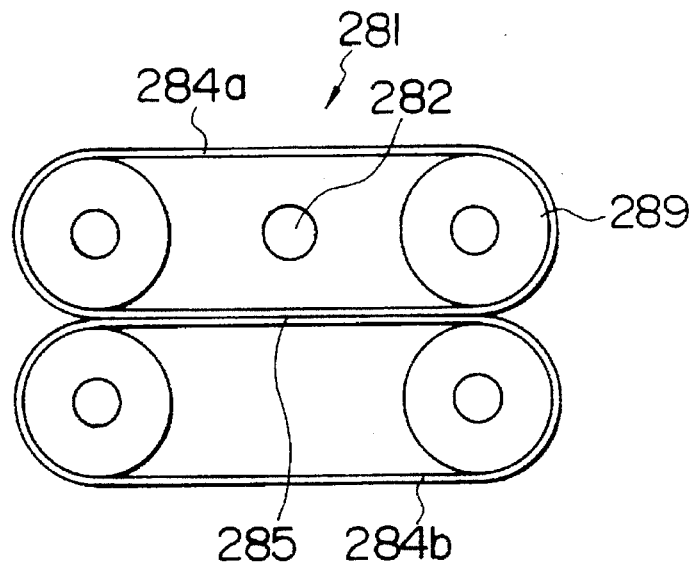

FIG. 20 shows other embodiment 281 of the present invention. In place of the heated roller 263 of the unit 261 of the embodiment shown in FIG. 18, a belt 284a is provided, and a bill 287 is held between the two belts 284a and 284b and transported thereby. A halogen lamp may be additionally arranged to face the belt 284b. In the present embodiment, the freedom of the shape and length of the heating unit 285 is increased.

Figure 21:
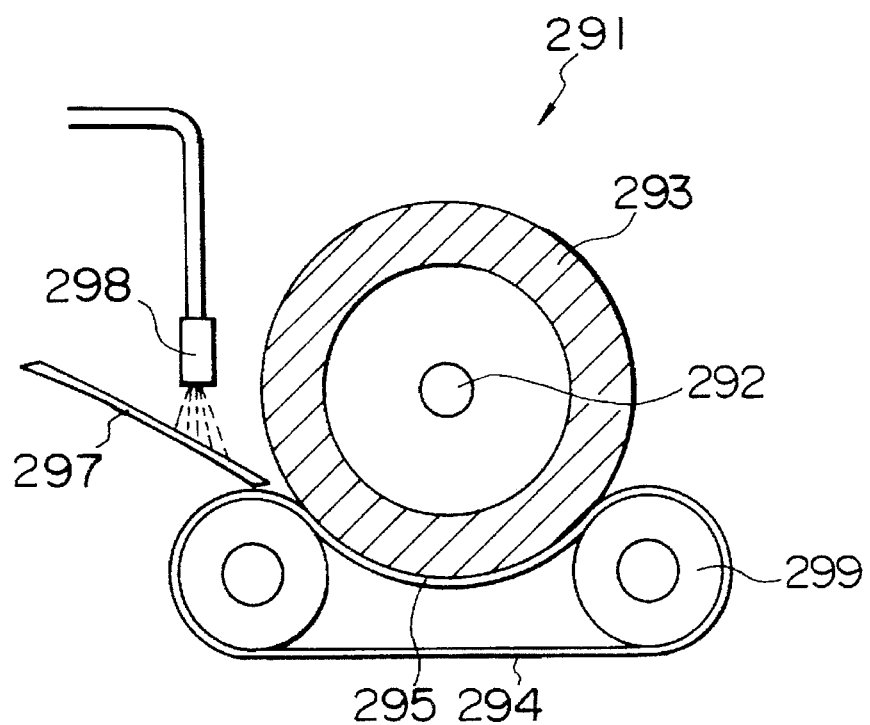
Figure 22:
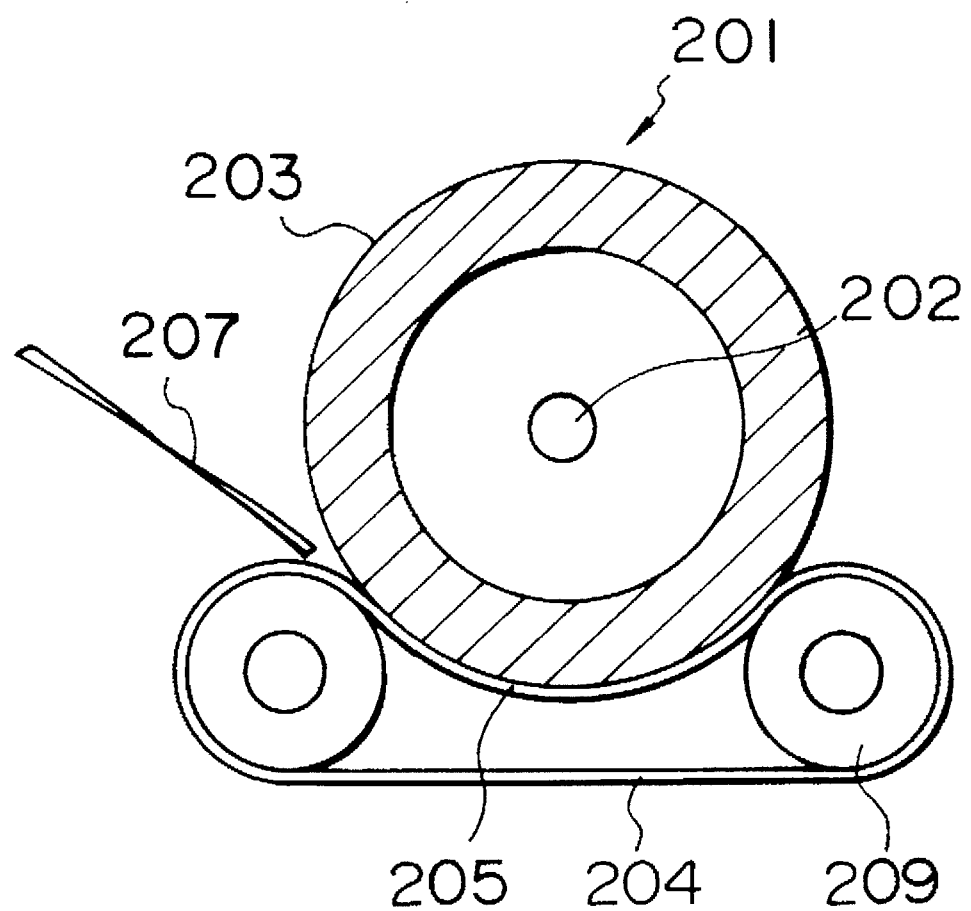

FIGS. 21 and 22 show other embodiments of the present invention. In a unit 291 of the embodiment shown in FIG. 21, a nozzle 298 for discharging water is arranged at the entry of the heating unit 265 of the unit 261 of the embodiment shown in FIG. 18. In a unit 201 of the embodiment shown in FIG. 22, a mercury lamp 202 is used in place of the heating halogen lamp 262 of the unit 261 of the embodiment shown in FIG. 18, and a heated roller 203 is made of a transparent material.

In the unit 291 of the embodiment shown in FIG. 21, the bill 297 fed into the heating unit 295 is applied with water by the nozzle 298 and then heated by the heating unit 295. As a result, the applied water is converted to high temperature water steam which disinfects and sterilizes the bill 297. In the unit 201 of the embodiment shown in FIG. 22, the heated roller 203 is made of silica having a high ultraviolet ray transmittance and the mercury lamp 202 having a high ultraviolet ray emission rate is provided in the heated roller 210. Accordingly, the bill 207 is exposed to the high temperature as well as a strong ultraviolet ray. As a result, the bill 207 is highly disinfected and sterilized.

Figure 23:
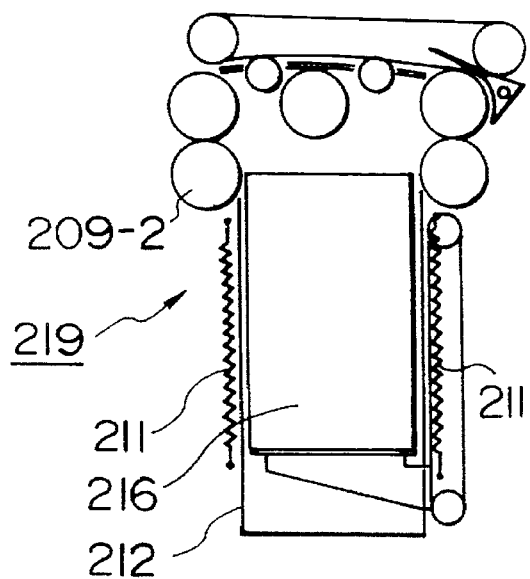
FIGS. 23 to 24 show schematic views of embodiments which disinfect moneys in denomination boxes, in which FIG. 23 uses a heater for heating, FIG. 24 uses electromagnetic wave irradiation for heating and FIG. 25 uses gas for disinfection.

An embodiment which has a disinfection unit in a denomination box is now explained. In the embodiment shown in FIG. 13, the disinfection unit is arranged in the transport unit 15. In the present embodiment, the disinfection units are arranged in the denomination boxes 209-1, 209-2 and 209-3 so that the bills are disinfected (including sterilization and pasteurization) while the bills are stored in the denomination boxes. FIG. 23 shows a specific embodiment. A heater 211 is arranged around a bill storage 212 of a denomination box 219 to heat the stored bills 216 in order to disinfect the bills.

Figure 24:
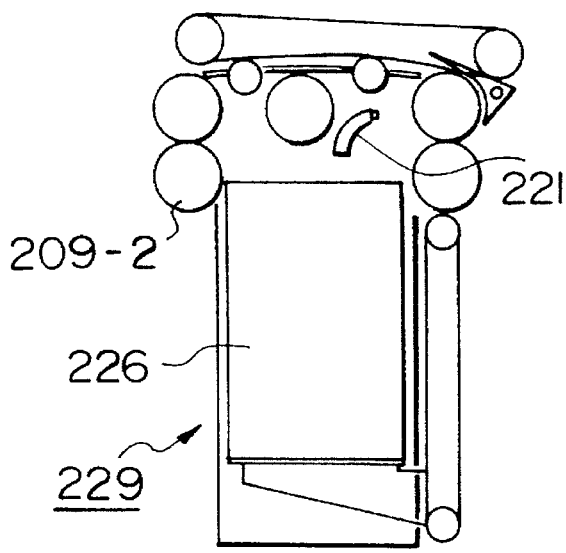

FIG. 24 shows an embodiment which heats the bills in a different manner. In the present embodiment, a microwave irradiation port 221 connected to a magnetron (not shown) is arranged on a denomination box 229 so that microscopes irradiates the bills 226 to heat and disinfect the bills. In FIG. 23, the bills are heated by the heater, and in FIG. 24, the bills are heated by the microwave. The heating method is not limited to those but, additionally hot air may be blown into the denomination box, for example.

Figure 25:
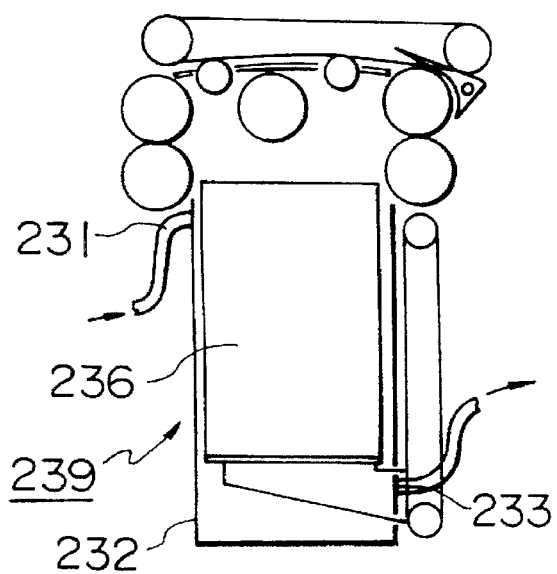

FIG. 25 shows another embodiment which disinfects (including sterilization and pasteurization) the bills while the bills are stored in the denomination box. A gas supply port 231 connected to a gas supply source (not shown) is provided in a storage 232 to fill the gas in the denomination box, and the gas which is effective to disinfect the bills 236 reacts with the bills. In the present embodiment, like in the embodiment shown in FIG. 16, gas recovery means may be provided to recover the gas filled in the storage to the gas supply source through the gas recovery port 236.

The disinfection means described above may have a bill deodorization effect by selecting the means and conditions to lower or stop the biochemical action which causes the bad smell.

Figure 26:
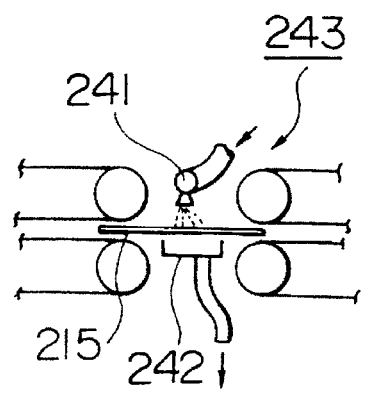
FIG. 26 shows a schematic view of an embodiment of a smell imparting device which gives smell to the money.

The automatic teller machine of FIG. 13 is provided with means 243 for imparting smell to the bills. FIG. 26 shows a specific embodiment for imparting smell. A nozzle 241 is provided closely to the transport path of the transport unit and volatile perfume is applied to the bills 215 from a supply source (not shown). By applying the volatile perfume to the bill 215 when it is transported to the receptacle 201, the smell may be imparted to the bill. Extra perfume is recovered by recovery means 242 and returned to the supply source.

In the above embodiments, the disinfection unit is arranged at the position shown in FIG. 13, but the disinfection (including sterilization and pasteurization) of moneys is effected in the following transactions (1) to (3).

(1) The bills thrown into the receptacle 201 are taken in, discriminated by the discrimination unit 204 and stored in the temporary store 206.

(2) The bills are taken out of the temporary store 206 after the above transaction, discriminated by the discrimination unit 204 and stored into the denomination box 209-1.

(3) The bills loaded in the cassette 211 are taken out by the temporary store 206, discriminated by the discrimination unit 204, and stored in the denomination box 209-1.

The disinfection unit may be arranged at the position of 210-2 in FIG. 13. In this case, the disinfection is effected when;

(4) the bills are taken out of the denomination boxes 209-1, 209-2 and 209-3, discriminated by the discrimination unit 204 and stacked in the receptacle 201, and (5) the money receiving transaction (2) and the supplement/load transaction (3) described above.

The disinfection unit may be arranged at the position 210-2 in FIG. 13. In this case, the disinfection is effected when;

(6) the bills are taken out of the denomination boxes 209-1, 209-2 and 209-3, discriminated by the discrimination unit 204 and stored into the cassette 211, and (7) the money counting transaction (1) described above.

The disinfection (including sterilization and pasteurization) means described above may be provided at any one of the positions 210, 210-1 and 210-2 in FIG. 13, or at any two positions or at three positions. The object of the present invention can also be achieved when they are provided at other position. The timing of the disinfection of the moneys may be in one of the transactions (1) to (7) or in a plurality of transactions. The moneys may also be disinfected during the checking of the moneys.

Figure 27:
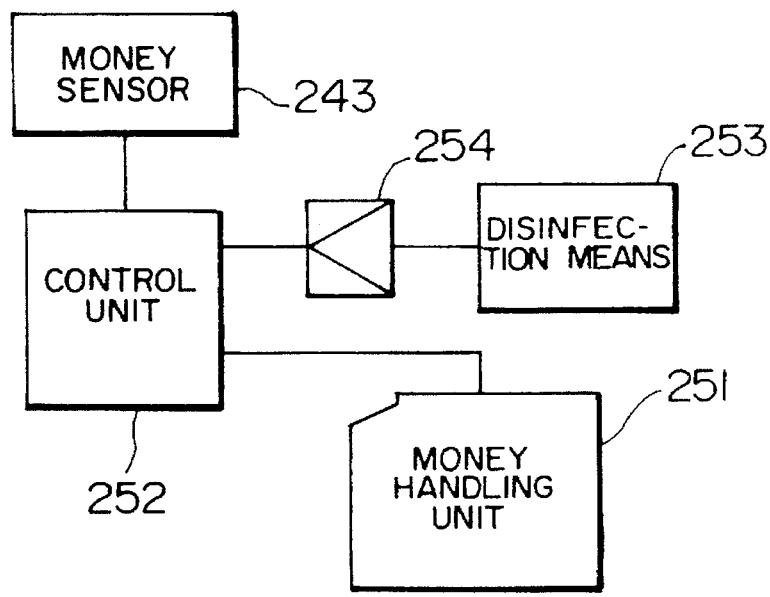
FIGS. 27 and 28 show block diagrams of a control unit which controls the machine of the present invention.

FIG. 27 shows a block diagram for explaining the control in the embodiment of the present invention. The bill handling unit 251 shown in FIG. 13 is controlled by a control unit 252, as it is in the exiting machine. The money disinfection means 253 is connected to the control unit 252 through a driven unit 254. The control unit 252 determines the start and stop timings of the disinfection means 253 in accordance with the transaction done by the money handling unit 251, the amount of bills stored, elapsed time and environmental conditions, and drives the disinfection means through the drive unit 254 in a manner to maximize the effect.

In order to attain full effect of the disinfection means which uses the ultraviolet ray lamp or the heated roller shown in FIGS. 14, 15 and 18 to 22, preheating may be required. The control unit 252 may always drive the heat supply source or drive it is response to the start of transaction caused by the user's manipulation.

In the embodiments of FIGS. 16 and 17 in which the ozone or drugs are applied, the disinfection unit is driven in timed relation with the transport of moneys. For example, as shown in FIG. 16, the money sensor 243 is arranged in front of the nozzle 241, the money detection signal from the money sensor 243 is sent to the control unit 252, which drives in response thereto.

Figure 28:
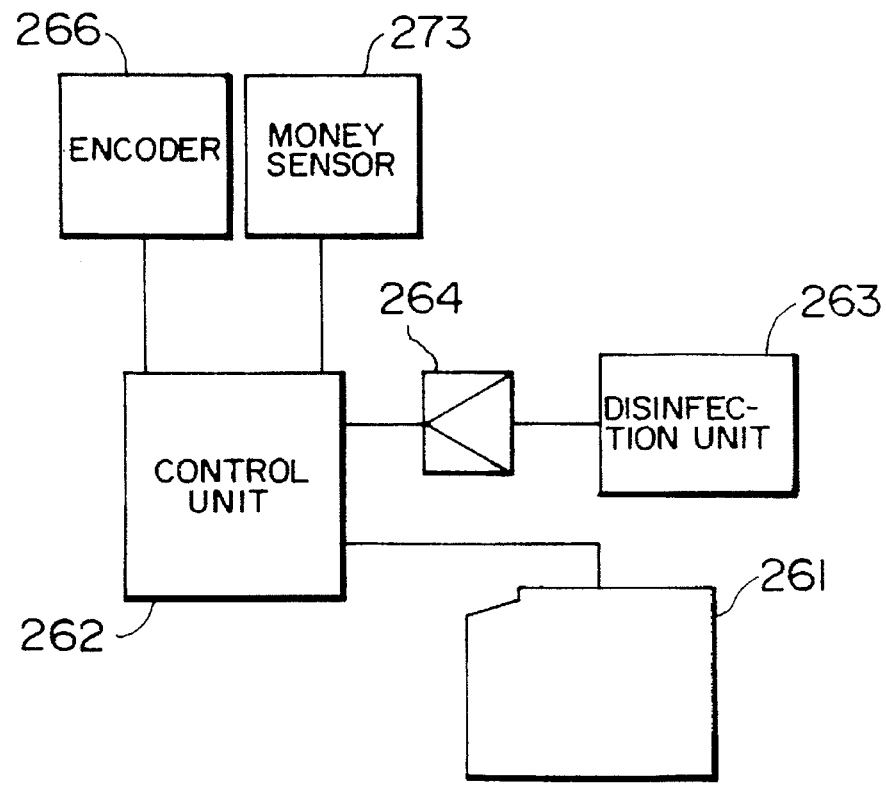

FIG. 28 shows a diagram for explaining another embodiment of the control. In the present embodiment, a money sensor 273 for detecting the passage of the money and an encoder 266 for encoding a displacement along the transport path are provided in the discrimination unit 204. When the money passes through the discrimination unit 204, the time of passage of the money is informed to the control unit 262 by the money sensor 273. The encoder 266 sends the encode signal so that the control unit determines the position of the transport path along which the money is transported and drives the disinfection unit 263 through the drive unit 264 in the timed relation with the passage of the money through the disinfection unit.

In the embodiments of FIGS. 211 and 212 in which the disinfection is effected in the denomination box, the disinfection unit may be always driven or driven periodically by a timer of the control unit.

The disinfection of the bills have been explained in the above embodiments, although the unit of the present invention is also applicable to coins. It may also be widely applicable to other than automatic teller machines such as automatic vending machine and automatic ticketing machine. The present invention is also applicable to the disinfection sterilization and pasteurization of other than bills, such as sheets.

While particular embodiments of the present invention have been shown and described, it will be obvious to those skilled in the art that various changes and modifications may be made without departing from the present invention in its broader aspects.

Figure 7:
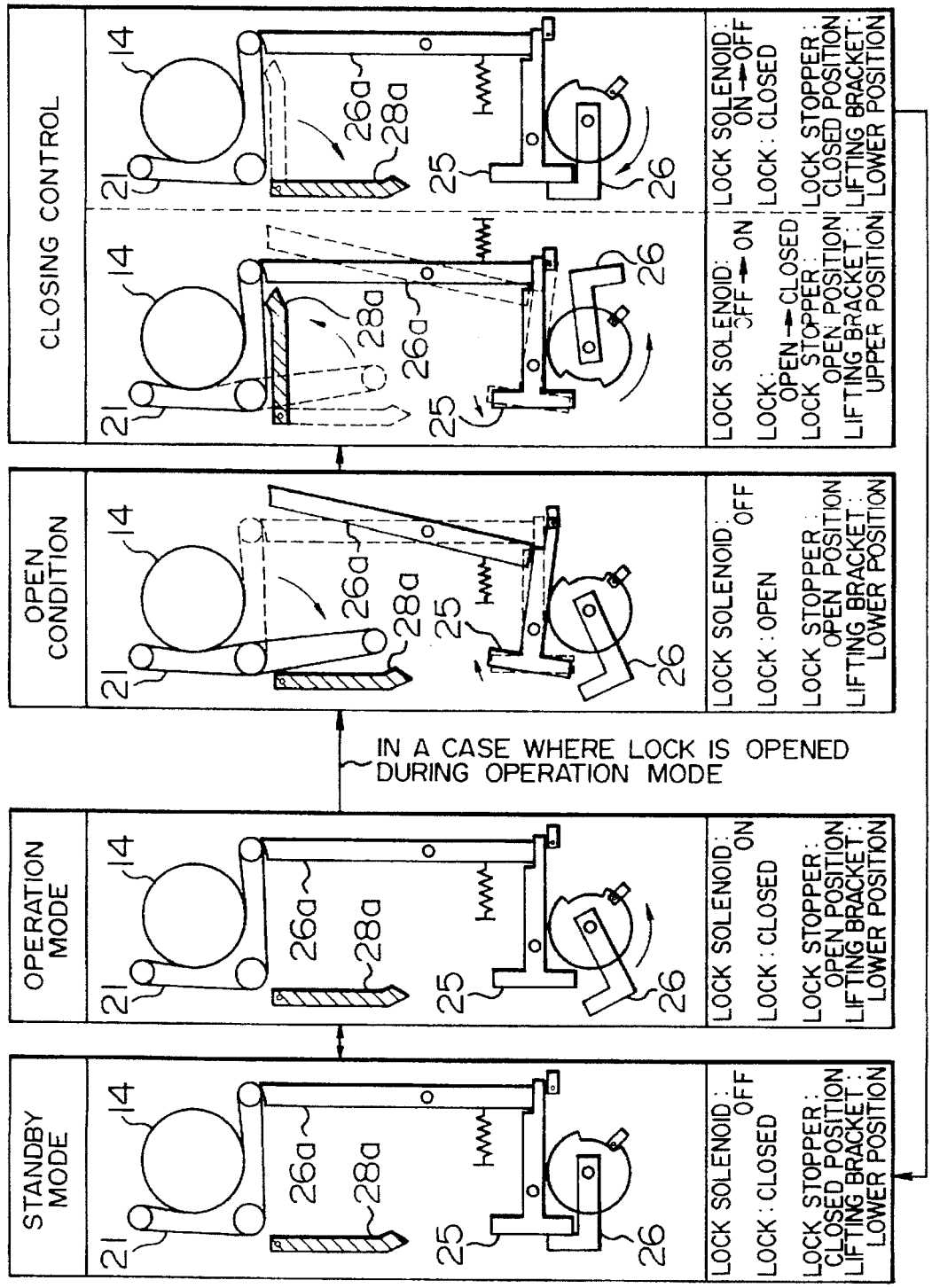
FIG. 7 is a diagram showing opening/closing control of the heat-resistant belt.

In the above embodiments, the process which is executed when bills are left untransported has been described with reference to FIGS. 2 and 7. The bills left untransported at the heating section 22 can be detected by a known detection method disclosed in JP-A-63-112350, for example. The method in JP-A-63-112350 is that two sensors for detecting passage of bills are provided on the transport path, and if a fixed time has passed since a bill passed the sensor on the upstream side of the transport path but the sensor on the downstream side does not detect the bill passing, it follows that the bill remaining untransported is detected by the two sensors. Thus, by installing two sensors on the input and output sides of the heating section 22, a bill remaining untransported at the heating section 22 can be detected. When a bill is left untransported at the heating section 22, if the heater 17 is turned OFF by the controller 19, safety is further ensured.

Figure 29:
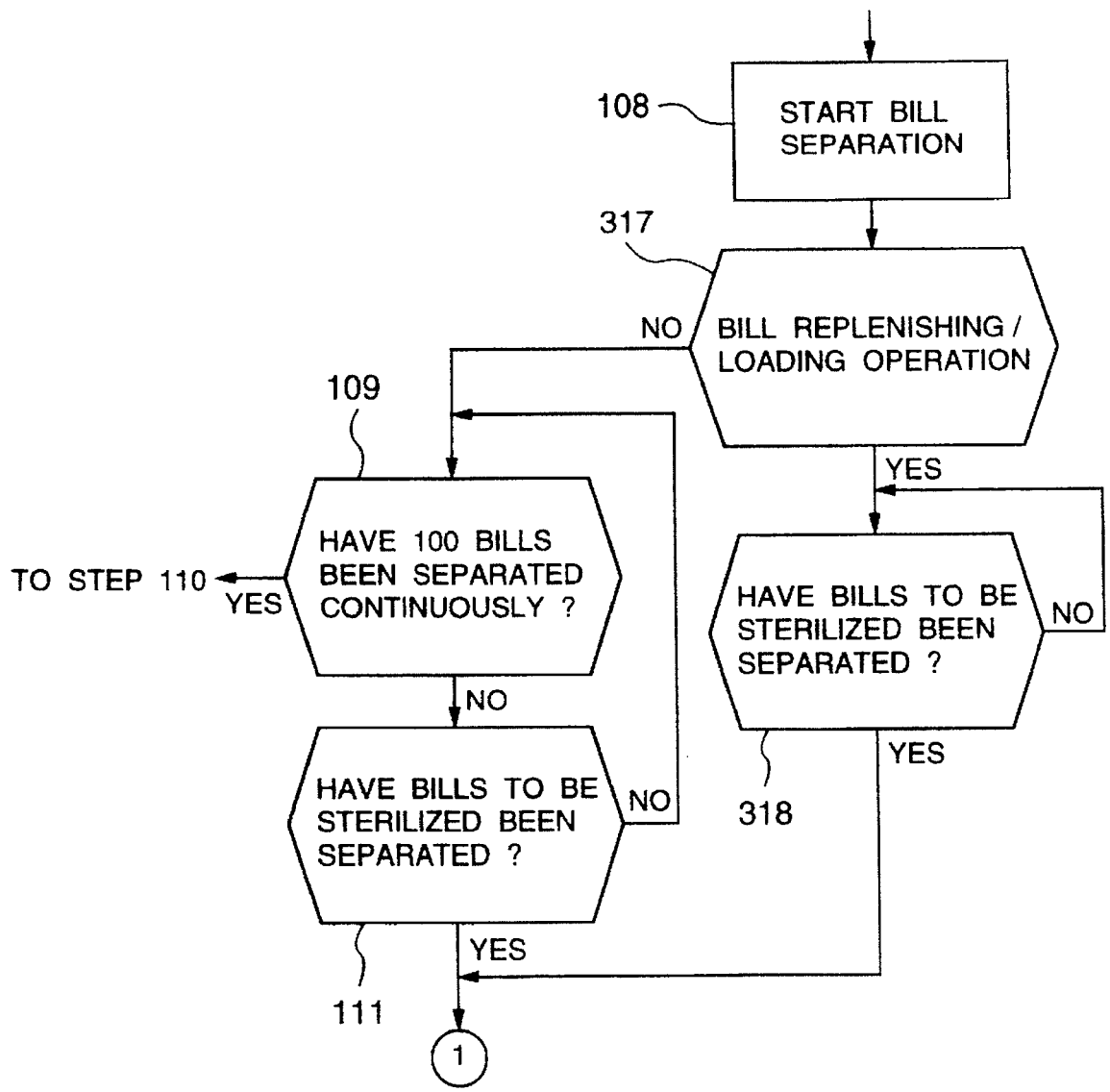
FIG. 29 is a flowchart showing the operation of another embodiment of the present invention.

FIG. 29 shows another embodiment of the present invention. In the embodiment shown in FIGS. 12A and 12B, in a transaction involving bill sterilization, each time a decision is made that 100 bills have been separated continuously at step 109, the separation is stopped at step 110, and the heated roller 14 is recovered to the holding temperature at step 104. In the embodiment in FIG. 29, steps 317 and 318 are added to the steps of FIGS. 12A and 12B. In the embodiment of FIG. 29, in the machine construction as shown in FIG. 6, instead of a decision whether or not a transaction involves bill sterilization in FIG. 12A, a decision is made whether the step is a "money receiving process in a money receiving transaction" and a "bill replenishing or loading operation".

In FIG. 29, when the bill separation is started (108), a decision is made whether the step is a bill replenishing or loading operation (317). If the step is not a bill replenishing or loading operation but a money receiving process in a money receiving transaction, the process moves on to step 318, and all bills are separated. In the embodiment in FIG. 29, control for temperature recovery at each continuous separation of 100 bills is not performed.

Description will now be made of an embodiment in which the heated roller is driven intermittently when bill sterilization is not carried out. In the examples shown in FIGS. 4, 5, 12A and 12B, the heated roller is driven at low speed when bill sterilization is not performed. That is rotational frequency of the heated roller decreases when bill sterilization is not performed.

As shown in FIG. 2, if a method of sterilizing bills by heating the heated roller 14 and the heat-resistant belt 21 wrapping around the heated roller to a high temperature and passing the bills between them, it is necessary to keep the heated roller and the heat-resistant belt uniformly at all times. To this end, the heated roller and the heat-resistant belts need to be rotated constantly. But, the means 20 for measuring the surface temperature of the heated roller, that is, a thermistor temperature sensor, for example, is pressed against the heated roller, for which reason the contact point of this temperature sensor will be worn and its service life will be shortened as the rotating distance of the heated roller becomes longer.

The heat-resistant belt itself has its life shortened when the number of flexings increases as the rotating distance thereof becomes longer. For instance, when the heat-resistant belt 21 is used as shown in FIG. 2, the number of flexings is four in total if three flex points by rollers and the portion of the belt pressed against the heated roller are put together. Therefore, as the cumulative number of revolution of the heated roller increases, the lives of the heater, heated roller, heat-resistant belt, thermistor temperature sensor, and gears, which constitute the bill sterilizing means, are shortened.

In this embodiment, by heating the heated roller and the heat-resistant belt so that their temperature is as uniform as possible, and by shortening the rotating distance of the heated roller and the heat-resistant belt, the lives of those component parts of the bill sterilizing means can be prolonged.

Figure 32:
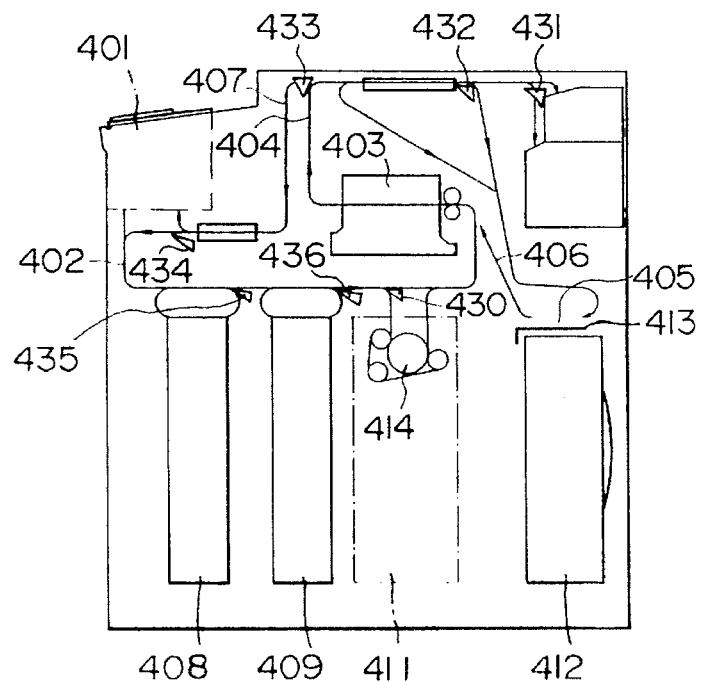
FIG. 32 is a general block diagram, in cross section, of the cash transaction machine in the present invention.

FIG. 32 is a block diagram, in cross section, of the bill transaction machine according to an embodiment of the present invention.

In a money receiving transaction, the user puts in bills at a receptacle 401. The bills put in are separated one by one by a separating mechanism, not shown, installed at the receptacle 401, and transported through a transport path 402 to a discrimination unit 403. The discrimination unit 403 discriminates the bills in terms of denomination, genuineness, damage, etc., and the bills are transported along a transport path 404, and stored in a temporary store unit.

If the transaction by the user's manipulation is realized, the bills stored in the temporary store unit 405 are separated by a separation unit, not shown, are again sent through the transport path 406 to the discrimination unit 403 for discrimination, and by passing through the transport paths 404, 407, and 402, the bills are transported into the denomination boxes for storage, classified by denominations, with which the money receiving transaction is finished.

On the other hand, in a money paying transaction, bills as many as the user requires are sent out of the denomination boxes 408, 409, separated one by one by a separation unit, not shown, and then put on the transport path 402.

When money is withdrawn, a gate 430 provided in the middle of the transport path 402 is switched to the side of the sterilizing unit 411, the bills are transported to the sterilizing unit 411, and while passing through the heated roller and the heat-resistant belt, each bill is sterilized, and after passing through the transport paths 402, 404 and 407, the bills are accumulated in the receptacle 401 and received by the user, then the paying transaction is finished.

In a money replenishing or loading operation, when the bills stored in the denomination boxes 408, 409 are running short, bills are set in a detachable bill cassette 412, a separator 413 is retracted, then the bills are sent out by the separation unit, not shown, from the bill cassette 412, transported through the transport path 406 to the discrimination unit 403, which determines the bills in terms of denominations, then the bills are carried by the transport paths 404, 407 and 402, and stored in the denomination boxes 408, 409.

As for a recovery operation, when either one of the denomination boxes 408, 409 is full, the bills are sent out of that denomination box, and after checked by the discrimination unit 403 in terms of denominations, the bills are stored in the bill cassette 412. All bills may be collected in the bill cassette 412. It is also possible to examine the balance of the bills in the machine by sequentially transporting the bills into the denomination boxes 408, 409 and the bill cassette 412 while passing the bills through the discrimination unit 403. The bills can be sterilized by switching the gate 430 of the transport path 402 in the above-mentioned collection or balance examination step.

Figure 30:
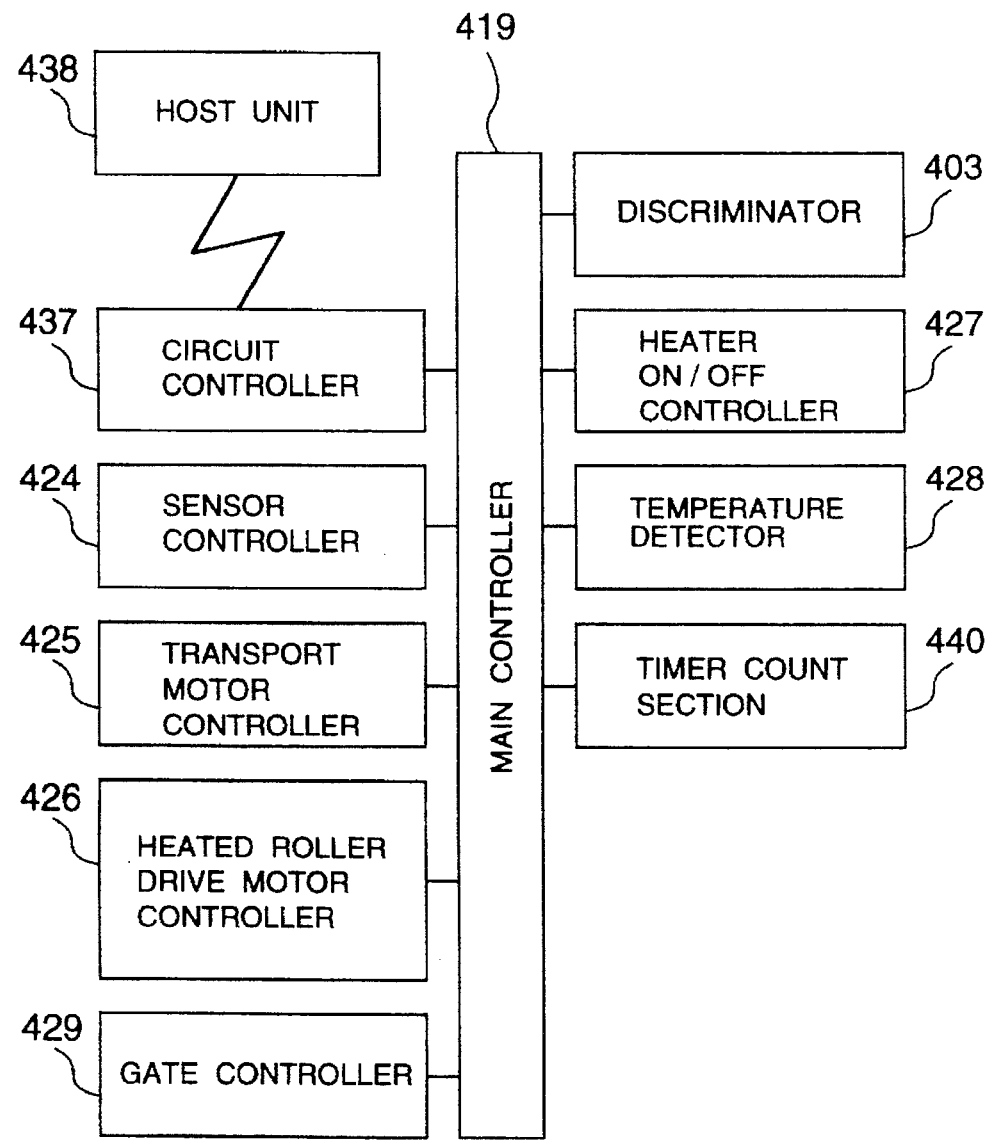
FIG. 30 is a block diagram of control of the cash transaction machine according to another embodiment of the present invention.
Figure 33:
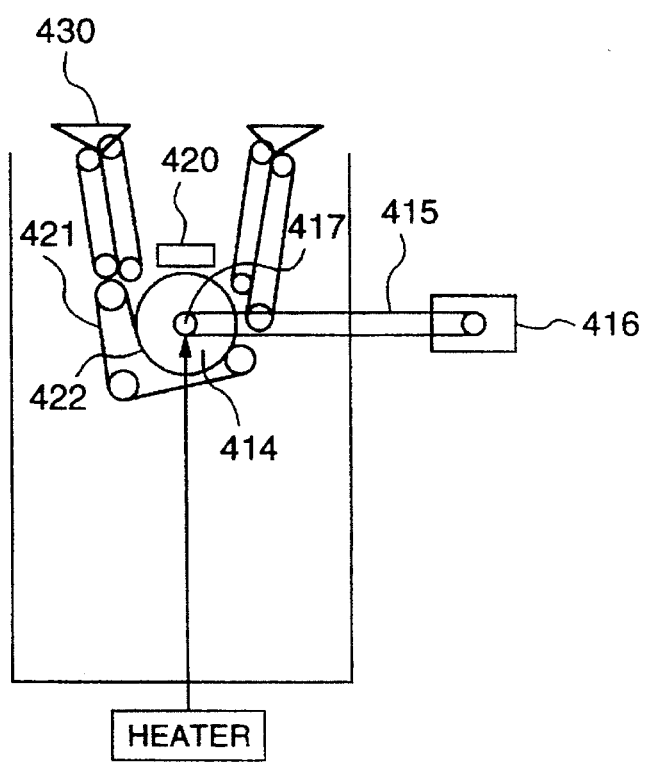
FIG. 33 is a diagram showing the sterilizing unit built in the cash transaction machine in the present invention.

FIG. 33 is a detailed block diagram of the sterilizing unit built in the bill transaction machine in FIG. 32. FIG. 30 is a control block diagram of the bill transaction machine in FIG. 32.

In FIG. 33, reference numeral 414 denotes a heated roller for heat-sterilizing the bills, supported by a rotary shaft, not shown, and connected to a motor 416 for driving the heated roller by a timing belt 415, so that the heated roller is driven to rotate by the heated roller drive motor 416. The heated roller drive motor 416 is a step motor, and is controlled by a heated roller drive motor controller 426 shown in FIG. 30 to change the rotating direction and rotating speed. Reference numeral 417 denotes an electric heater to heat the heated roller 414, and the heater generates a calorific value to keep the surface temperature of the heated roller 414 at a sterilizing temperature or higher, and is controlled by a heater ON/OFF controller 427 shown in FIG. 30. Reference numeral 420 denotes a temperature sensor to measure the surface temperature of the heated roller 414, and though the temperature sensor appears to be separated from the heated roller 414, it is actually pressed on the heated roller. Temperature data obtained by the temperature sensor 420 is input to a temperature detector 428 of FIG. 30 and sent to the main controller 419.

On the basis of temperature data sent from the temperature detector 428, the main controller 419 issues a command to the heater ON/OFF controller 427 directing it to turn on or off the electric heater 417, and thus the surface temperature of the heated roller 414 is controlled so as to be normally at the above-mentioned holding temperature, that is, 185° C. to 190° C., for example.

Reference numeral 421 denotes a heat-resistant belt wrapping around the heated roller 414, and the belt has a tension applied which is required to sterilize the bills. The section 422 where the heat-resistant belt 421 and the heated roller 414 are in contact with each other is the bill heating section. As the heated roller 414 and the heat-resistant belt 421 are rotated, the bills having entered the heating section 422 are heat-sterilized while they are transferred.

A sensor controller 424 in FIG. 30 read signals from a plurality of sensors which watch bills passing or remaining on the transport path, and detect that the actuator and the like are located at specified positions. The sensor controller 424 sends signals to the main controller 419.

A transport motor controller 425 turns on and off a motor to drive the transport path in response to a command from the main controller 419. A discrimination unit 340 discriminates the bills in terms of denomination, genuineness, damage, and other necessary items, and notifies results to the main controller 419. A gate controller 429 turns on and off gates 430, 431, 432, 433, 434, 435, and 436 in response to commands from the main controller 419 to thereby switch the destinations of the bills. On receiving a command to receive or dispense money or the like from the host unit 438, that is, from an ATM main body, for example, a circuit controller 437 sends this information to the main controller 419 or receives a result of the operation from the main controller 419 and sends the result to the host unit 438.

Reference numeral 440 denotes a timer count section which monitors the stop time of the heated roller drive motor 416 and causes the stop time to be decremented at fixed periods.

As for the heat-resistant belt 421 in FIG. 33, if the heated roller drive motor 416 is rotated at fixed speed continuously, the heat-resistant belt 421 and the heated roller 414 contact at different portions thereof, so that the heat-resistant belt 421 can be made uniformly warm. In this case, however, the heated roller drive motor 416 is kept rotating and, therefore, the temperature sensor 420 has its life shortened as the rotating distance become longer. In addition, as the rotating distance of the heat-resistant belt 421 becomes longer, the number of its flexings increases and its life becomes shorter.

In the case of the sterilizing unit shown in FIG. 33, the heat-resistant belt 421 is flexed at a total of four points: three points by direction-changing rollers and a contact section where the belt is in contact with the heated roller 414, with the result that as the heat-resistant belt rotates, the number of times of flexings will increase.

In order to shorten the rotating distance and prolong the life of the heat-resistant belt, an intermittent operation of the heated roller is performed when a transaction does not involve bill sterilization. The time when bill sterilization is not performed is the same as in the case shown in FIG. 12A, that is, in transactions in which bills are not sterilized or when the machine is in a stand-by state. When the bills are not sterilized, the heated roller is controlled so as to be at a holding temperature of 185° C. to 190° C. as described with reference to FIG. 12A.

Figure 31:
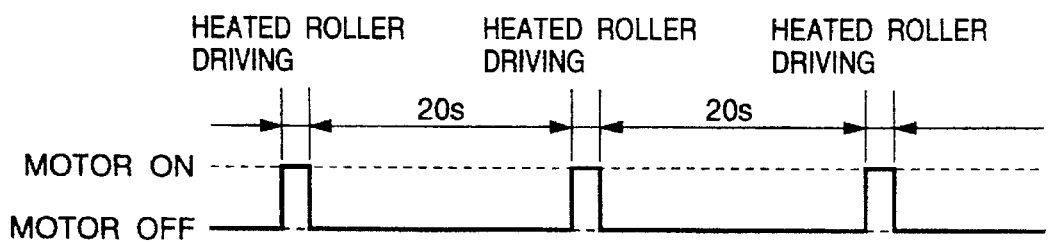
FIG. 31 is a time chart of a heated roller drive motor in the intermittent operation in the present invention.

FIG. 31 is a time chart of the operation of the heated roller drive motor in FIG. 33. In other words, FIG. 31 shows the ON and OFF states of the heated roller drive motor 416 when the heated roller 414 is driven intermittently.

The heated roller drive motor 416 which has been stationary is driven at an adequate drive timing, and then the heated roller drive motor 416 is stopped at an adequate stop timing. This procedure is repeated in the intermittent operation.

In this embodiment (FIG. 33), about ¼ of the heat-resistant belt 421 is in contact with the heated roller 414, and the heat-resistant belt 421 is rotated for a ¼ of one revolution as the heated roller drive motor 416 makes one revolution. Accordingly, while the heated roller drive motor 416 makes three revolutions, the heat-resistant belt 421 makes ¾ of one revolution, and by performing an intermittent operation four times, the whole of the heat-resistant belt 421 is heated. After a stoppage for 20 sec., the heated roller drive motor 416 is started and driven for three revolutions and stopped again.

It may be satisfactory if the heat-resistant belt is rotated in steps of ¼ of one revolution. But, in rotating the heat-resistant belt, it is necessary to take into consideration a possibility that the pulse motor does not rotate correctly. Therefore, the pulse motor is rotated intermittently in such a way that it makes three revolutions a time so that the portion of the heat-resistant belt which is in contact with the heated roller may be shifted, on an average, by ¼ of the whole belt length in one movement of the belt which corresponds to three motor revolutions of the motor.

Figure 34:
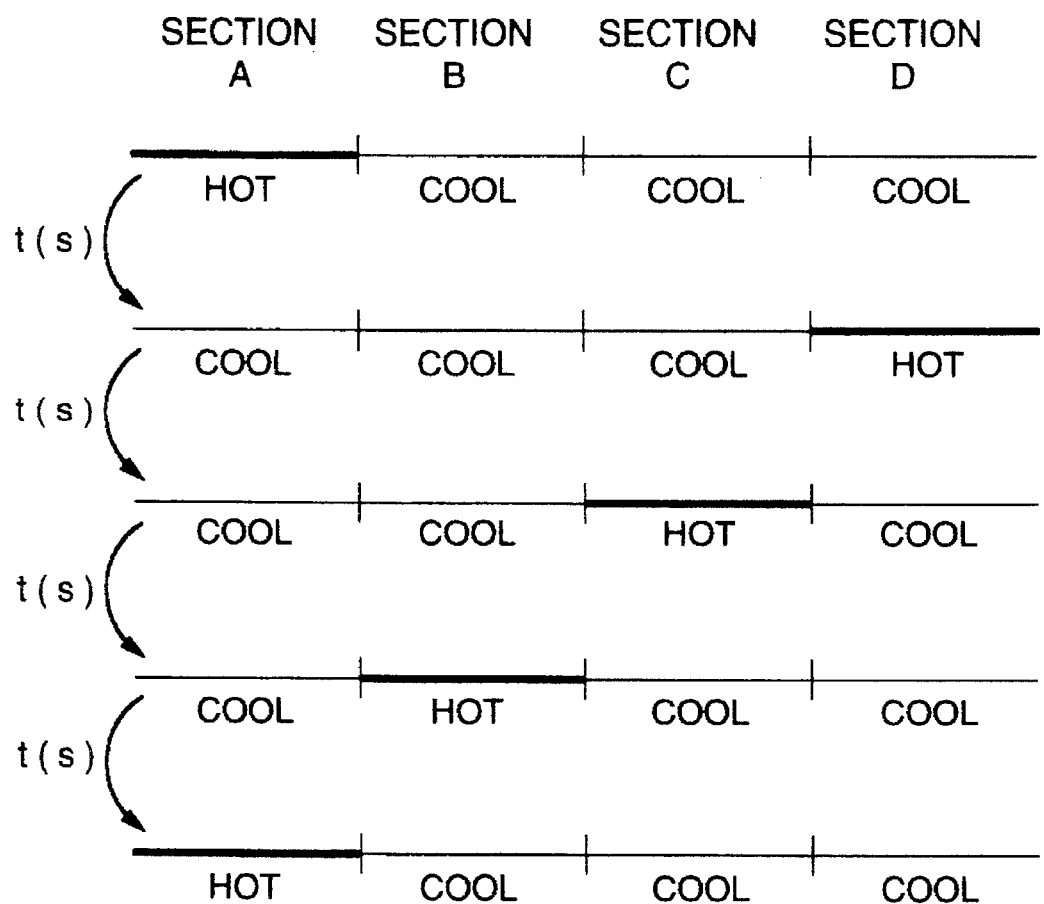
FIG. 34 is a diagram showing the condition of various parts of the heat-resistant belt in the intermittent operation in the present invention.
Figure 35:
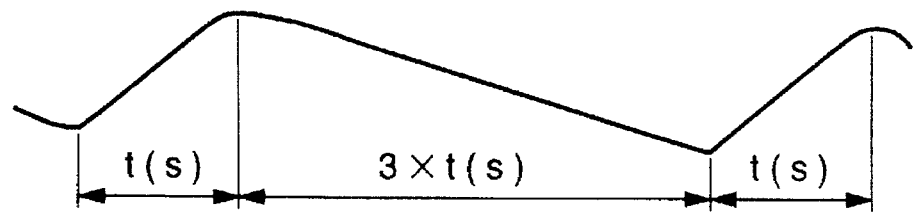
FIG. 35 is a diagram showing temperature changes of a certain part of the heat-resistant belt in the intermittent operation in FIG. 18.

FIG. 34 is a diagram showing the hot/cold condition of each portion of the heat-resistant belt 421 in the intermittent operation of the heated roller in FIG. 33. FIG. 35 is a diagram showing changes of temperature in a certain portion of the heat-resistant belt in the intermittent operation.

If the heat-resistant belt 421 is divided into four sections, section A, section B, section C and section D, the changes of state proceed in phases as shown from the top toward the bottom of FIG. 34. In FIG. 34, the drive timing of intermittent operations is designated as t sec., and the bold lines show the heated portions. To take the section A for example, after heated for t sec., the section A radiates heat for the following 3×t sec. and then heated again for t sec. Likewise, one after another, the sections B, C and D are heated for t sec., and after a heat radiation period of 3 t sec, they are heated again for t sec.

The temperature of the section A changes as shown in FIG. 35. After heating for t sec., the heat is dissipated for 3 t sec., and because of this, the temperature difference between the upper limit value and the lower limit value for the section A is decided by the value of t. Therefore, the upper limit value and the lower limit value of temperature in this case is decided without direct relation to the sterilizing temperature of the bills. To be more specific, the temperature difference is greater for a greater t and smaller for a smaller t. In this embodiment, if t is set at 20 sec., the changes of temperature of the section A is included within the range of temperature required for sterilization.

For this reason, in this embodiment, the stop timing is set subsequent to 3 revolutions after the heated roller drive motor is driven and the drive timing is set 20 sec. after the motor is stopped.

By adopting the intermittent operation, the stop time of the heated roller 414 occupies the greater part of the operating time, for which reason the life of the temperature sensor 420 pressed against the heated roller is made longer than in the continuous operation.

As has been described, the characteristics differ between the intermittent operation and the continuous operation.

In order to prolong the life of the temperature sensor 420, the intermittent operation is advantageous, but in the intermittent operation, it is necessary to have the heat-resistant belt 421 warmed uniformly to heat-sterilize the bills transferred to the heating section.

Only when the bill sterilization process is to be performed and the heat-resistant belt 421 is to be warmed uniformly, the heated roller drive motor 416 is driven continuously at fixed speed, but driven intermittently on other occasions. In this way, the uniform warming of the heat-resistant belt 421 and the life prolongation of the temperature sensor 420 are made compatible.

Figure 36:
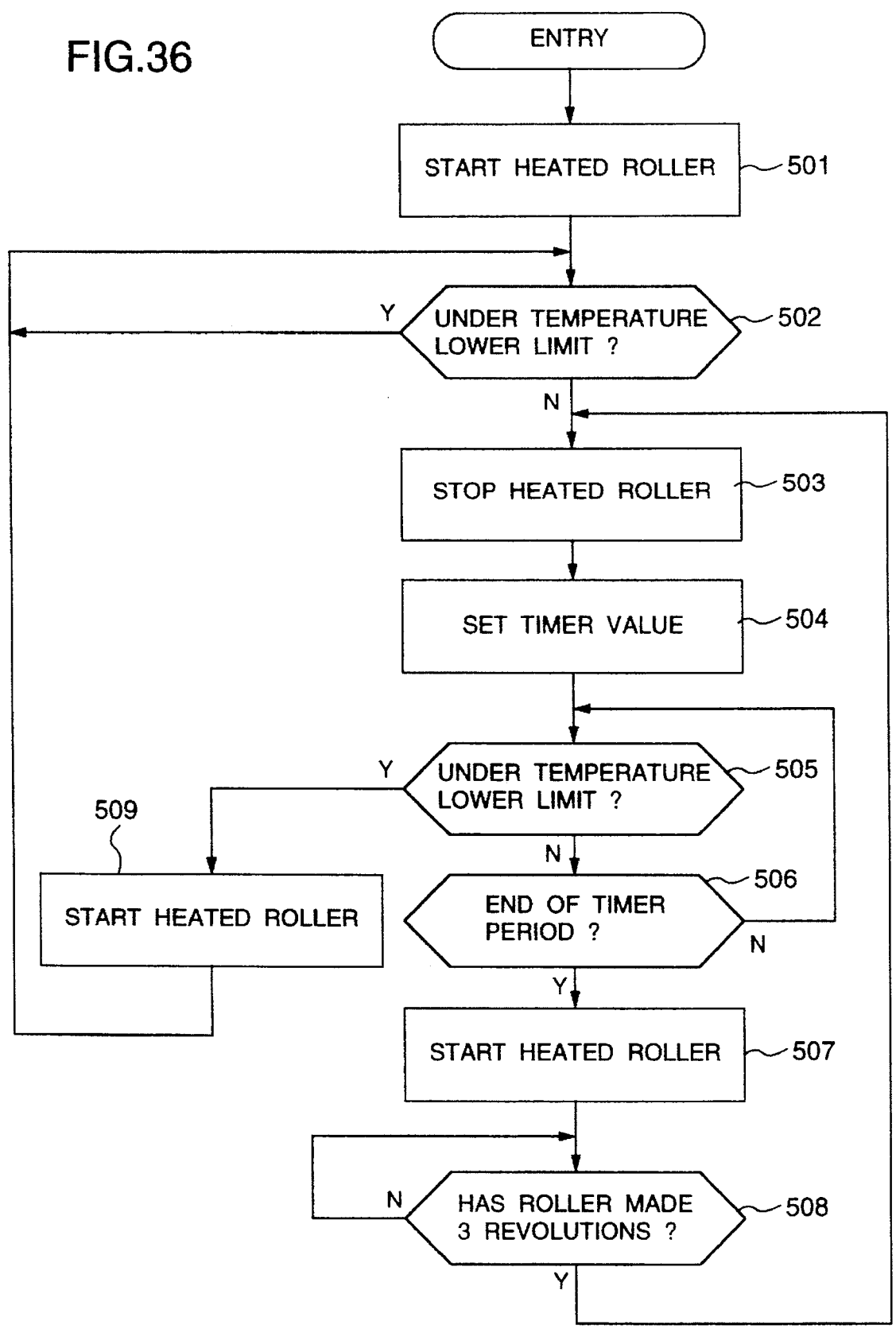
FIG. 36 is a control flowchart of the heated roller when sterilization of bills is not performed in the present invention.
Figure 37:
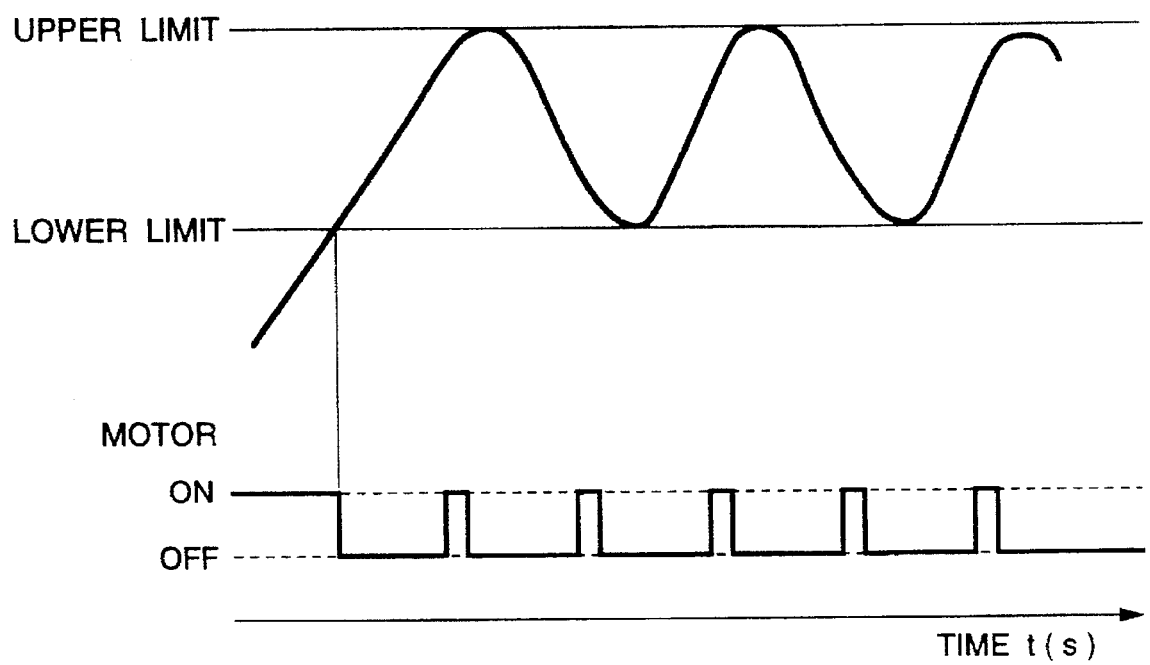
FIG. 37 is another time chart of the heated roller in FIG. 36.

FIG. 36 is a control flowchart of the heated roller when the bill sterilization is not performed. FIG. 37 is a time chart showing the relation between the heated roller temperature during the bill sterilization, and the ON and OFF states of the heated roller drive motor.

The ON/OFF control of the motor according to the surface temperature of the heated roller 414 will be described with reference to the control block diagram in FIG. 30 and the control flow in FIG. 36.

When starting the heated roller 414, the main controller 419 issues a command to start the heated roller drive motor 416 to the heated roller drive motor controller 426 and, consequently, the heated roller 414 is started (step 501). The temperature detector 428 constantly receives temperature data from the temperature sensor 420, and derives the data to the main controller 419. The main controller 419 checks if the received temperature data reaches the temperature lower limit value (step 502), and does not issue a command to the heated roller drive motor controller 426 until the lower limit is reached, thus letting the heated roller 414 continue the current operation. When the received temperature data reaches the lower limit value, the main controller 419 issues a command to stop the heated roller drive motor 416 to the heated roller drive motor controller 426, thus causing the heated roller 414 to stop (step 503). The main controller 419 causes the monitoring time stored in the memory of the main controller 419 to be set in the timer area of the timer count section 440 (step 504). The timer count section 440 causes the timer which has been set to be decremented at fixed periods.

The main controller 419 issues commands to turn on and off the electric heater 417 to the heater ON/OFF controller 427 in order that the heated roller 414 is held between the upper limit value and the lower limit value of the holding temperature.

After time has been set on the timer, the main controller 419 checks if the received temperature data is under the lower limit value (step 505). If the temperature data is not under the lower limit, the value in the timer area is checked (step 506). If the monitoring timer has not reached the end of the timer period, the temperature lower limit value and the value in the timer area are checked again (step 505). If the monitoring timer reaches the end of the timer period before the temperature data falls under the lower limit value (step 506), the main controller 419 issues a command to start the heated roller drive motor 416 to the heated roller drive motor controller 426 (step 507). The main controller 419 calculates the number of revolutions of the heated roller drive motor 416 from sensor data from the sensor controller 424, and when the specified number (three revolutions in this embodiment) is reached (step 508), the main controller 419 issues a command to stop the heated roller drive motor 416 to the heated roller drive motor controller 426, thus causing the heated roller 414 to stop (step 503). Next, the monitoring time stored in the memory in the main controller 419 is set in the timer area of the timer count section 440 (step 504).

The above-mentioned checks of the temperature lower limit value and the value in the timer area are repeated until the temperature data falls under the lower limit value (step 505).

When the temperature data falls under the lower limit value (step 505), the main controller 419 issues a command to drive the heated roller drive motor 416 to the heated roller drive motor controller 426 (step 509). Like at starting, while the temperature is under the lower limit value, the heated roller 414 is driven continuously (step 502). The above operation is repeated.

In FIG. 37, if the temperature is as low as when power is first supplied, the temperature is checked by the temperature sensor to see if it rises up to the lower limit of the holding temperature, and while the temperature is under the lower limit of the holding temperature, the heated roller is driven at constant speed. When the temperature rises up to the upper limit of the holding temperature, the heated roller is driven intermittently. As for the drive timing in the intermittent operation, after driven for a specified distance from a given time, the heated roller is stopped, and this operation is repeated. The ON/OFF control of the heated roller is performed by both control by the lower limit value of the holding temperature and timing control, after all. Whichever occurs earlier does the control. In the case of FIG. 37, the timer reaches the end of the timer period before the temperature lower limit value is reached, and for this reason, the motor is turned on and off by timing control. As is clear from the ON and OFF times of the motor in FIG. 37, the motor is controlled so that the stop time of the motor is longer.

Figure 38:
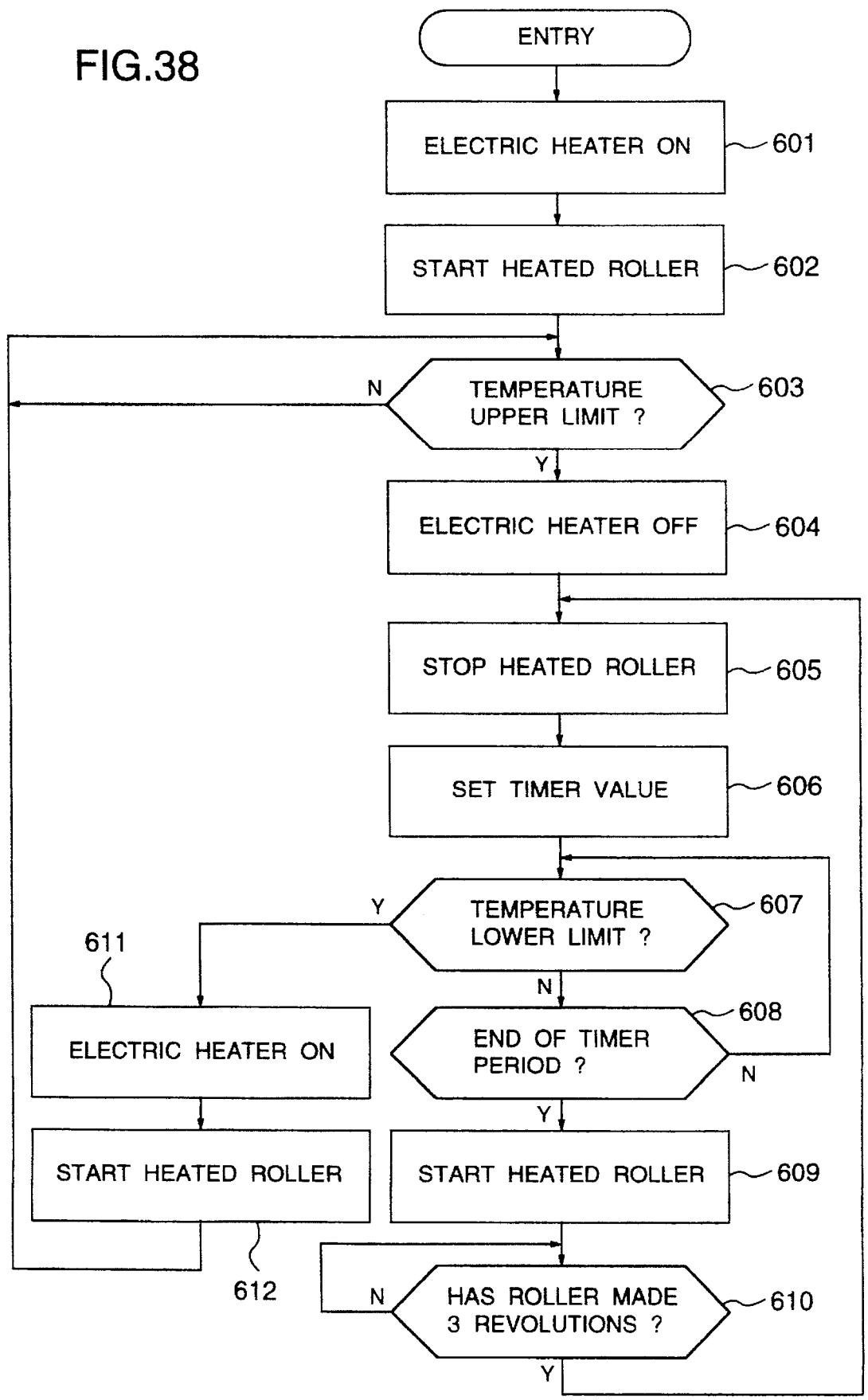
FIG. 38 is another control flowchart of the heated roller when the sterilization of bills in the present invention.
Figure 39:
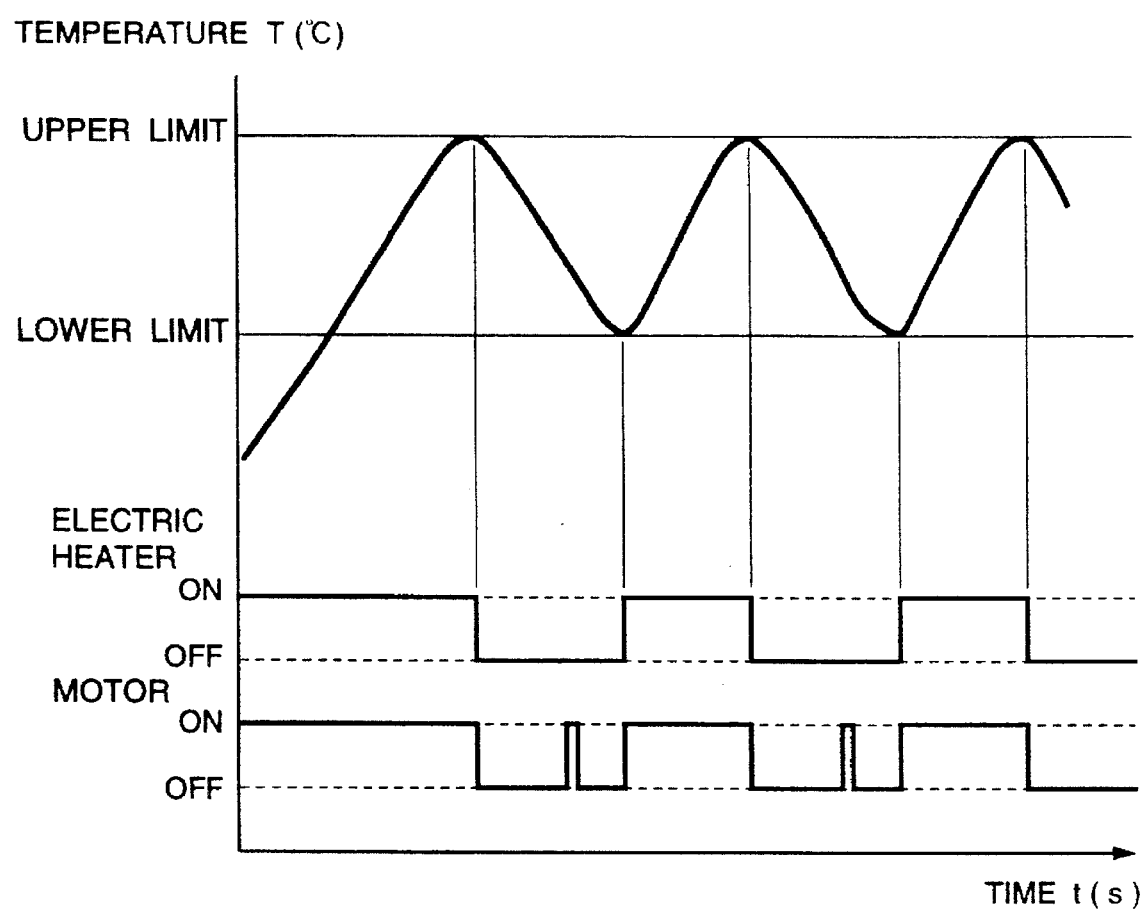
FIG. 39 is yet another time chart of the heated roller in FIG. 38.

FIG. 38 is a control flowchart when the bill sterilization is not performed, of the heated roller and the electric heater in another embodiment of the present invention. FIG. 39 is a time chart showing the relation between the heated roller temperature in this embodiment, and the ON and OFF states of the heated roller drive motor and the electric heater.

The ON/OFF control of the motor in compliance with the states of the heater in the present invention will be described with reference to the control block diagram in FIG. 30 and the control flow in FIG. 38.

The main controller 419 issues a command to turn on the electric heater 417 to the heater ON/OFF controller 427 (step 601), and also issues a command to start the heated roller drive motor 416 to the heated roller drive motor controller 426 (step 602).

The temperature detector 428 constantly receives temperature data from the temperature sensor 420, and derives the data to the main controller 419. The main controller 419 checks if the received temperature data reaches the upper limit value of the holding temperature (this period is hereafter referred to as waiting for the temperature upper limit value)(step 603), and does not issue a command to the heater ON/OFF controller 427 and the heated roller drive motor controller 426 until the upper limit is reached, letting the heated roller 414 and the electric heater 417 continue the current operations. When the received temperature data reaches the lower limit value (step 603), the main controller 419 issues a command to turn off the electric heater 417 to the heater ON/OFF controller 427 (step 604), and also issues a command to stop the heated roller drive motor 416 to the heated roller drive motor controller 426, thereby stopping the heated roller 414 (step 605). Then, the main controller 419 causes the heating monitoring time stored in the memory of the main controller 419 to be set in the timer area of the timer count section 440 (step 606). The timer count section 440 decrements the timer, which has been set, at fixed periods.

Thereafter, the temperature of the heated roller 414 and the heat-resistant belt 421 decreases, and the temperature data of the temperature sensor 420 detected by the temperature detector 428 decreases accordingly.

The main controller 419 checks if the received temperature data reaches the temperature lower limit value (step 607), and if the temperature data has not reached the lower limit value, checks the value in the timer area (step 608). If the monitoring timer has not reached the end of the timer period, the main controller 419 checks the temperature lower limit value and the value in the timer area again (step 607). If the monitoring timer reaches the end of the timer period before the temperature data goes down to the temperature lower limit value (step 608), the main controller 419 issues a command to start the heated roller drive motor 416 to the heated roller drive motor controller 426 (step 609). The main controller 419 calculates the number of revolutions of the heated roller drive motor 416 from sensor data from the sensor controller 424, and when the specified number (three revolutions in this embodiment) is reached (step 610), the main controller issues a command to stop the heated roller drive motor 416 to the heated roller drive motor controller 426, thus stopping the heated roller 414 again (step 605). The main controller 419 causes the heating monitoring time stored in the memory of the main controller 419 to be set in the timer area of the timer count section 440 (step 606).

The above-mentioned checks of the temperature lower limit value and the value of the timer area are repeated until the temperature data reaches the lower limit value (steps 607, 608).

When the temperature data reaches the temperature lower limit value (step 607), the main controller 419 issues a command to turn on the electric heater 417 to the heater ON/OFF controller 427 (step 611), and also issues a command to start the heated roller drive motor 416 to the heated roller drive motor controller 426 (step 612). The steps from waiting for the temperature upper limit value onwards are repeated (step 603).

According to this embodiment, when the bills are not sterilized, more specifically, when the transaction is of a kind which does not involve bill sterilization or when the machine is in a stand-by state, the heated roller 414 is held at the holding temperature, and while the heated roller 414 and the heat-resistant belt 421 are heated uniformly, the rotation distance of the heated roller 414 can be made shorter than in the continuous rotation. Therefore, the lives of the temperature sensor 420 and the heat-resistant belt 421, which are always in contact with the heated roller 414 can be prolonged.

In FIG. 39, monitoring is performed to see if the electric heater is on, and when the heater is turned on, the heated roller is driven at constant speed, and if the heater is turned off, the heated roller is driven intermittently. As for the drive timing in the intermittent drive, after the heated roller has run a specified distance from a given time, for example, the heated roller is stopped. This operation is repeated. When electric heater is turned on again, the heated roller is driven in a constant-speed rotation. The heated roller is controlled to turn on and off when the upper and the lower limit values are reached.

By this arrangement, the heated roller operates with better efficiency, so that the lives of the temperature sensor and the heat-resistant belt are prolonged, and the periods until those parts are replaced are prolonged. By adopting the intermittent operation, the stop time of the motor occupies the greater part of the operating time, which contributes to a reduction of noise.

In the case of FIG. 39, the heated roller is heated until the temperature upper limit value, so that the whole of the heat-resistant belt is warmed to the sterilizing temperature. The end of the preset timer period is reached before the temperature lower limit value is reached, for which reason, only the motor is turned on once by timing control before the lower limit is reached and after making three revolutions, the pulse motor is stopped and when the temperature falls to the lower limit value, the pulse motor is turned on again. As is clear by a look at the ON and OFF times of the motor shown in FIG. 39, in this case the motor is controlled so that the driving time is long.

We claim:

1. A cash transaction machine, comprising:

a receptacle for depositing and withdrawing bills;

storing means for storing said bills;

transporting means for transporting said bills between said receptacle and said storing means;

sterilizing means for transferring said bills to and from said transport means, and heat-sterilizing said bills;

temperature detecting means for sensing a temperature of said sterilizing means; and control means for controlling an execution of transaction performed in the cash transaction machine according to a temperature detected by said temperature detecting means.

2. A cash transaction machine according to claim 1, wherein said control means includes means for controlling a heating temperature of said sterilizing means so as to be in a specified temperature range according to the temperature detected by said temperature detecting means.

3. A cash transaction machine according to claim 1, wherein said control means limits the number of bills to be sterilized continuously.

4. A cash transaction machine according to claim 1, wherein said sterilizing means includes a heated roller, heating transport means for transferring said bills by pressing said bills against said heated roller for at least a predetermined angle range, and heating means for heating said heated roller, and wherein said control means for giving a signal to drive said heated roller and said heating transfer means even when the bill sterilization is not performed.

5. A cash transaction machine according to claim 4, wherein said control means reduces rotational frequency of said heated roller and said heating transfer means when the bill sterilization is not performed.

6. A cash transaction machine according to claim 4, wherein said control means gives a signal to rotate said heated roller and said heating transfer means at low speed when the bill sterilization is not performed.

7. A cash transaction machine according to claim 1, wherein said sterilizing means comprises a heated roller, driving means for driving a heated roller in a continuous or an intermittent operation in response to a signal from said control means, heating transfer means for transferring said bills while pressing said bills against said heated roller for at least a predetermined angle range, and heating means for heating said heated roller, wherein said control means gives a signal to cause said driving means to rotate continuously when a transaction involves the bill sterilization, and gives a signal to cause said driving means to rotate intermittently in transactions other than a transaction involving the bill sterilization.

8. A cash transaction machine according to claim 1, wherein said sterilizing means includes a heated roller, heating transfer means for transferring said bills while pressing said bills against said heated roller at least for a predetermined angle range, heating means for heating said heated roller, a jam sensor for detecting if said bills are left untransferred at said sterilizing means, and means for removing said bills from said heated roller, wherein said control means actuates said removing means when said jam sensor detects said bills remaining untransferred.

9. A cash transaction machine according to claim 8, wherein said removing means is formed by means for moving said transfer means to a position away from said heated roller.

10. A cash transaction machine according to claim 9, wherein said removing means further includes means for blowing sufficient air to said heated roller to remove said bills.

11. A cash transaction machine according to claim 8, wherein said control means controls said heating means to stop heating when said jam sensor detects a jamming of said bills.

12. A method of sterilizing bills in a cash transaction machine including a receptacle for depositing and withdrawing bills; storing means for storing said bills; transporting means for transporting said bills between said receptacle and said storing means; and sterilizing means for transferring said bills to and from said transport means and heat-sterilizing said bills, comprising the steps of:

controlling a temperature of said sterilizing means so as to be in a specified range;

starting a transport of bills by said transport means if said temperature of said sterilizing means is within said range when a command is given to perform a transaction involving bill sterilization; and detecting if the temperature of said sterilizing means is within said range each time a predetermined number of bills are transported, and if the temperature is within said range, transporting a following predetermined number of bills.

13. A method of sterilizing bills in a cash transaction machine including a receptacle for depositing and withdrawing bills; storing means for storing said bills; transporting means for transporting said bills between said receptacle and said storing means; and sterilizing means for transferring said bills to and from said transport means, and heat-sterilizing said bills, comprising the steps of:

controlling a temperature of said sterilizing means so as to be in a specified range; and starting a transport of bills by said transport means if the temperature of said sterilizing means is within said range when a command is given to perform a transaction involving bill sterilization.

14. A method of sterilizing bills in a cash transaction machine including a receptacle for depositing and withdrawing bills; storing means for storing said bills; transporting means for transporting said bills between said receptacle and said storing means; and sterilizing means for transferring said bills to and from said transport means, and heat-sterilizing said bills, comprising the steps of:

controlling a temperature of said sterilizing means so as to be in a specified range;

starting a transport of bills by said transport means if the temperature of said sterilizing means is within said range when a command is given to perform a transaction involving bill sterilization;

when, a first kind of transaction involving bill sterilization is performed, detecting if the temperature of said sterilizing means is within said range each time a predetermined number of bills are transported, and if the temperature is within said range, transporting a following predetermined number of bills; and when, a second kind of transaction involving bill sterilization is performed, continuously transporting bills regardless of the number of bills to be transported;

wherein said first kind of transaction is a bill receiving transaction, and said second kind of transaction is a bill replenishing or loading operation.

15. A cash transaction machine, comprising:

a receptacle for depositing and withdrawing bills;

storing means for storing said bills;

transporting means for transporting said bills between said receptacle and said storing means;

heating means for transferring said bills to and from said transport means, and heating said bills;

temperature detecting means for sensing a temperature of said heating means; and control means for controlling an execution of transaction performed in the cash transaction machine according to a temperature detected by said temperature detecting means.

16. A cash transaction machine according to claim 15, wherein said control means includes means for controlling a heating temperature of said heating means so as to be in a specified temperature range according to the temperature detected by said temperature detecting means.

17. A cash transaction machine according to claim 15, wherein said control means limits the number of bills to be heated continuously.

18. A cash transaction machine according to claim 15, wherein said heating means includes a heated roller, a heating transfer means for transferring said bills by pressing said bills against said heated roller for at least a predetermined angle range, and heating means for heating said heated roller, and wherein said control means for giving a signal to drive said heated roller and said heating transfer means even when heating is not performed.

19. A cash transaction machine according to claim 18, wherein said control device reduces rotational frequency of said heated roller and said heating transfer means when heating is not performed.

20. A cash transaction machine according to claim 18, wherein said control means issues a signal to rotate said heated roller and said heating transfer means at low speed when sterilization is not performed.

21. A cash transaction machine according to claim 15, wherein said heating means comprises a heated roller, driving means for driving a heated roller in a continuous or an intermittent operation in response to a signal from said control means, heating transfer means for transferring said bills while pressing said bills against said heated roller for at least a predetermined angle range, and a heater for heating said heated roller, wherein said control means gives a signal to cause said driving means to rotate continuously when a transaction involves heating, and gives a signal to cause said driving means to rotate intermittently in transactions other than a transaction involving heating.

22. A cash transaction machine according to claim 15, wherein said heating means includes a heated roller, heating transfer means for transferring said bills while pressing said bills against said heated roller at least for a predetermined angle range, a heater for heating said heated roller, a jam sensor for detecting if said bills are left untransferred at said sterilizing means, and means for removing said bills from said heated roller, wherein said control means actuates said removing means when said jam sensor detects said bills remaining untransferred.

23. A cash transaction machine according to claim 22, wherein said removing means is formed by means for moving said transfer means to a position away from said heated roller.

24. A cash transaction machine according to claim 23, wherein said removing means further includes means for blowing sufficient air to said heated roller to remove said bills.

25. A cash transaction machine according to claim 22, wherein said control means controls said heating means to stop heating when said jam sensor detects a jamming of said bills.

26. A method of heating bills in a cash transaction machine including a receptacle for depositing and withdrawing bills; storing means for storing said bills; transporting means for transporting said bills between said receptacle and said storing means; and heating means for transferring said bills to and from said transport means and heating said bills, comprising the steps of:

controlling a temperature of said heating means so as to be in a specified range;

starting a transport of bills by said transport means if said temperature of said heating means is within said range when a command is given to perform a transaction involving heating; and detecting if the temperature of said heating means is within said range each time a predetermined number of bills are transported, and if the temperature is within said range, transporting a following predetermined number of bills.

27. A method of heating bills in a cash transaction machine including a receptacle for depositing and withdrawing bills; storing means for storing said bills; transporting means for transporting said bills between said receptacle and said storing means; and heating means for transferring said bills to and from said transport means and heating said bills, comprising the steps of:

controlling a temperature of said heating means so as to be in a specified range; and starting a transport of bills by said transport means if the temperature of said heating means is within said range when a command is given to perform a transaction involving heating.

28. A method of heating bills in a cash transaction machine including a receptacle for depositing and withdrawing bills; storing means for storing said bills; transporting means for transporting said bills between said receptacle and said storing means; and heating means for transferring said bills to and from said transport means and heating said bills, comprising the steps of:

controlling a temperature of said heating means so as to be in a specified range;

starting a transport of bills by said transport means if the temperature of said heating means is within said range when a command is given to perform a transaction involving heating;

when, a first kind of transaction involving heating is performed, detecting if the temperature of said heating means is within said range each time a predetermined number of bills are transported, and if the temperature is within said range, transporting a following predetermined number of bills; and when, a second kind of transaction involving heating is performed, continuously transporting bills regardless of the number of bills to be transported;

wherein said first kind of transaction is a bill receiving transaction and said second kind of transaction is a bill replenishing or loading operation.

29. A cash transaction machine, comprising:

a receptacle for depositing and/or withdrawing bills;

a denomination box for storing said bills;

a sterilizer for sterilizing said bills;

transporter for transferring said bills among said receptacle, said denomination box and said sterilizer;

a sensor for detecting a temperature of said sterilizer; and means for controlling execute of transaction in said transaction machine by referring to said temperature of said sterilizer detected by said sensor.

30. A cash transaction machine, comprising:

a receptacle for depositing and/or withdrawing bills;

a denomination box for storing said bills;

a sterilizer for sterilizing or disinfecting said bills, said sterilizer comprises a roller having heated surface, and an endless belt facing said heated surface of roller for pressing said bills therebetween for a fixed angle or more;

a transporter for transferring said bills among said receptacle, said denomination box and said sterilizer;

a temperature sensor for sensing a temperature of said heated surface of said roller;

a heat controller for controlling said temperature of said heated surface at a predetermined temperature range by referring to said temperature detected by said temperature sensor;

a jam sensor for sensing whether said bills are in untransported situation within said sterilizer;

a rejecter for rejecting said bills from said heated surface of roller when said jam sensor senses that said bills are in untransported situation;

a controller for decreasing rotational frequency of said roller and said endless belt when said jam sensor senses that said bills are in untransported situation; and a limiter for limiting a number of said bills to be processed by said sterilizer.

31. A cash transaction machine, comprising:

a receptacle for depositing and/or withdrawing bills;

a denomination box for storing said bills;

a heater for heating said bills at predetermined temperature range;

transporter for transferring said bills among said receptacle, said denomination box and said heater;

a sensor for detecting a temperature of said sterilizer; and means for controlling execute of transaction in said transaction machine by referring to said temperature of said heater detected by said sensor.

32. A cash transaction machine, comprising:

a receptacle for depositing and/or withdrawing bills;

a denomination box for storing said bills;

a heater for heating said bills, said heater comprises a roller having heated surface, and an endless belt facing said heated surface of roller for pressing said bills therebetween for a fixed angle or more;

a transporter for transferring said bills among said receptacle, said denomination box and said heater;

a temperature sensor for sensing a temperature of said heated surface of said roller;

a heat controller for controlling said temperature of said heated surface at a predetermined temperature range by referring to said temperature detected by said temperature sensor;

a jam sensor for sensing whether said bills are in untransported situation within said heater;

a rejecter for rejecting said bills from said heated surface of roller when said jam sensor senses that said bills are in untransported situation;

a controller for decreasing rotational frequency of said roller and said endless belt when said jam sensor senses that said bills are in untransported situation; and a limiter for limiting a number of said bills to be processed by said heater.

33. A cash transaction machine, comprising:

a receptacle for depositing and withdrawing bills;

storing means for storing said bills;

transport means for transporting said bills between said receptacle and said storing means;

heating means for transferring said bills to and from said transport means and heating said bills;

gate means for switching whether to direct said bills being transported by said transport means towards said heating means, or to let said bills bypass said heating means; and control means for switching over said gate means according to a kind of transaction to be performed in said cash transaction machine.

34. A cash transaction machine according to claim 33, wherein said heating means is sterilizing means for sterilizing said bills by heating.

35. A cash transaction machine according to claim 33, wherein said heating means for pressing said bills to substantially remove folds and rumples thereof.

36. A cash transaction machine for executing a plurality of transactions, comprising:

a receptacle for receiving and/or dispensing said bills;

storing means for storing said bills;

transport means for transporting said bills between said receptacle and said storing means;

heating means for transferring said bills to and from said transport means and heating said bills;

gate means for switching whether to direct said bills being transported by said transport means towards said heating means, or to let said bills bypass said heating means; and control means for switching over said gate means to direct said bills toward said heating means when at least one predetermined specific transaction of said plurality of transactions is executed.

37. A cash transaction machine according to claim 36, wherein said heating means presses said bills to substantially remove folds and rumples thereof.

38. A cash transaction machine according to claim 36, wherein said heating means sterilizes said bills by heating.

39. A cash transaction machine according to claim 36, wherein said predetermined specific transaction is a bill receiving transaction.

40. A cash transaction machine, comprising:

a first path through which bills are transferred;

a heater for heating said bills;

a second path, along which said heater is installed, for receiving said bills from said first path for heating, and sending heated bills back to said first path;

a gate on said first path for selecting said first path or said second path to which said bills be transferred in accordance with a kind of transaction executed in said cash transaction machine.

41. A machine according to claim 40, further comprising means for applying a pressure to said bills to remove folds and rumples thereof in cooperate with said heater.

42. A machine according to claim 40, wherein said gate selects said second path in a bill receiving transaction.

* * * * *